United States Patent
Jelicich et al.

(10) Patent No.: US 11,158,046 B2
(45) Date of Patent: Oct. 26, 2021

(54) ESTIMATING MEASUREMENTS OF CRANIOFACIAL STRUCTURES IN DENTAL RADIOGRAPHS

(71) Applicant: Overjet, Inc., Allston, MA (US)

(72) Inventors: Alexander Albert Joseph Jelicich, Citrus Heights, CA (US); Wardah Inam, Boston, MA (US); Deepak Ramaswamy, Newton, MA (US)

(73) Assignee: Overjet, Inc., Allston, MA (US)

( * ) Notice: Subject to any disclaimer, the term of this patent is extended or adjusted under 35 U.S.C. 154(b) by 98 days.

(21) Appl. No.: 16/752,362

(22) Filed: Jan. 24, 2020

(65) Prior Publication Data

US 2021/0233233 A1    Jul. 29, 2021

(51) Int. Cl.
| | |
|---|---|
| G06K 9/00 | (2006.01) |
| G06T 7/00 | (2017.01) |
| G06T 7/11 | (2017.01) |
| G06T 7/70 | (2017.01) |
| G06T 7/80 | (2017.01) |
| G16H 10/60 | (2018.01) |

(52) U.S. Cl.
CPC ............ *G06T 7/0012* (2013.01); *G06T 7/11* (2017.01); *G06T 7/70* (2017.01); *G06T 7/80* (2017.01); *G16H 10/60* (2018.01); *G06T 2207/10124* (2013.01); *G06T 2207/20081* (2013.01); *G06T 2207/20084* (2013.01); *G06T 2207/20172* (2013.01); *G06T 2207/30008* (2013.01); *G06T 2207/30036* (2013.01); *G06T 2207/30052* (2013.01)

(58) Field of Classification Search
CPC . G06T 7/0012; G06T 7/80; G06T 7/11; G06T 7/70; G06T 2207/10124; G06T 2207/20081; G06T 2207/20084; G06T 2207/20172; G06T 2207/30008; G06T 2207/30036; G06T 2207/30052; G16H 10/60
USPC ............................................... 382/128
See application file for complete search history.

(56) References Cited

U.S. PATENT DOCUMENTS

| | | | |
|---|---|---|---|
| 5,416,822 A | 5/1995 | Kunik | |
| 7,292,674 B2 | 11/2007 | Lang | |
| 9,033,576 B2 | 5/2015 | Yankelevitz et al. | |
| 9,283,061 B2 * | 3/2016 | Tank | G06T 7/149 |
| 9,710,603 B2 * | 7/2017 | Kaminski | A61C 19/00 |
| 10,074,178 B2 * | 9/2018 | Cocco | G06F 19/00 |
| 10,248,883 B2 * | 4/2019 | Borovinskih | G06T 7/32 |

(Continued)

FOREIGN PATENT DOCUMENTS

EP      2976746 B1     1/2016

*Primary Examiner* — Jonathan S Lee
(74) *Attorney, Agent, or Firm* — Occhiuti & Rohlicek LLP

(57) ABSTRACT

A method and system for receiving a dental radiographic image that includes an oral structure, and in an image processor, selecting a segmenter and an object detector, predicting masks and points of the oral structure using the segmenter and the object detector to become part of image metadata. The dental radiographic image and image metadata are further provided to a measurement processor for selecting at least one measurement method of a set of measurement methods according to the dental radiographic image and the image metadata, calculating a sensor pixel to mm (millimeter) ratio using the measurement method, and calculating a calibrated measurement of the oral structure.

18 Claims, 19 Drawing Sheets

(56) References Cited

U.S. PATENT DOCUMENTS

| | | | | |
|---|---|---|---|---|
| 10,390,913 B2* | 8/2019 | Sabina | | A61C 9/0053 |
| 10,482,204 B2* | 11/2019 | Marie | | G06K 9/6253 |
| 11,037,671 B2* | 6/2021 | Kaminski | | G16H 40/63 |
| 2016/0225151 A1* | 8/2016 | Cocco | | G06F 16/51 |
| 2016/0371412 A1* | 12/2016 | Marie | | G01D 4/002 |
| 2017/0049311 A1* | 2/2017 | Borovinskih | | G06T 5/20 |
| 2019/0231490 A1* | 8/2019 | Sabina | | A61B 1/00009 |

* cited by examiner

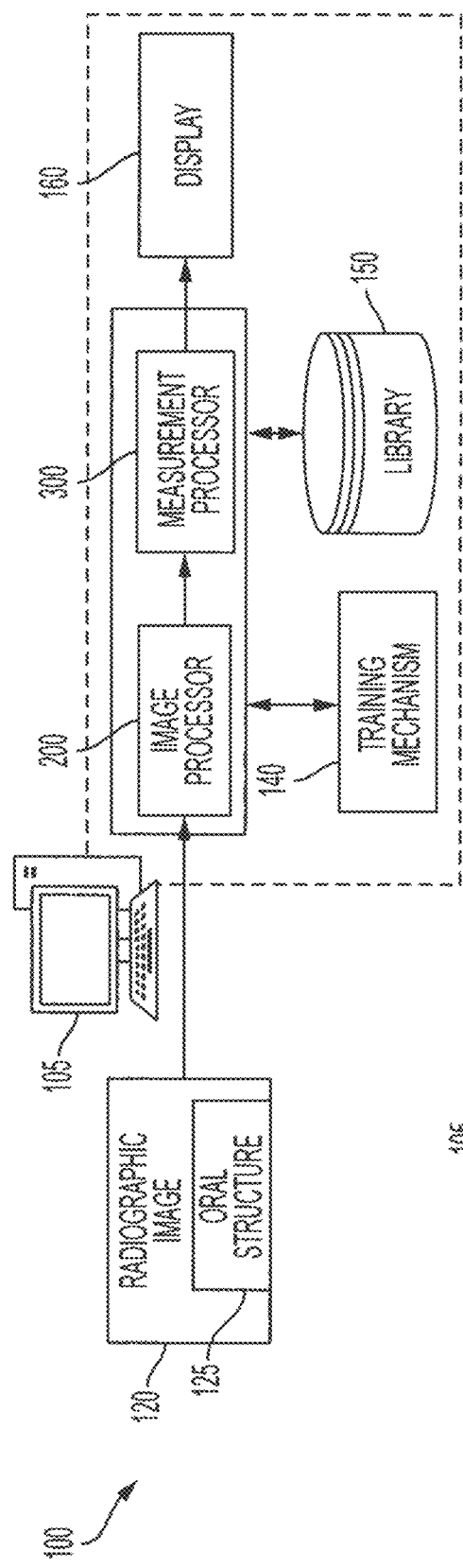
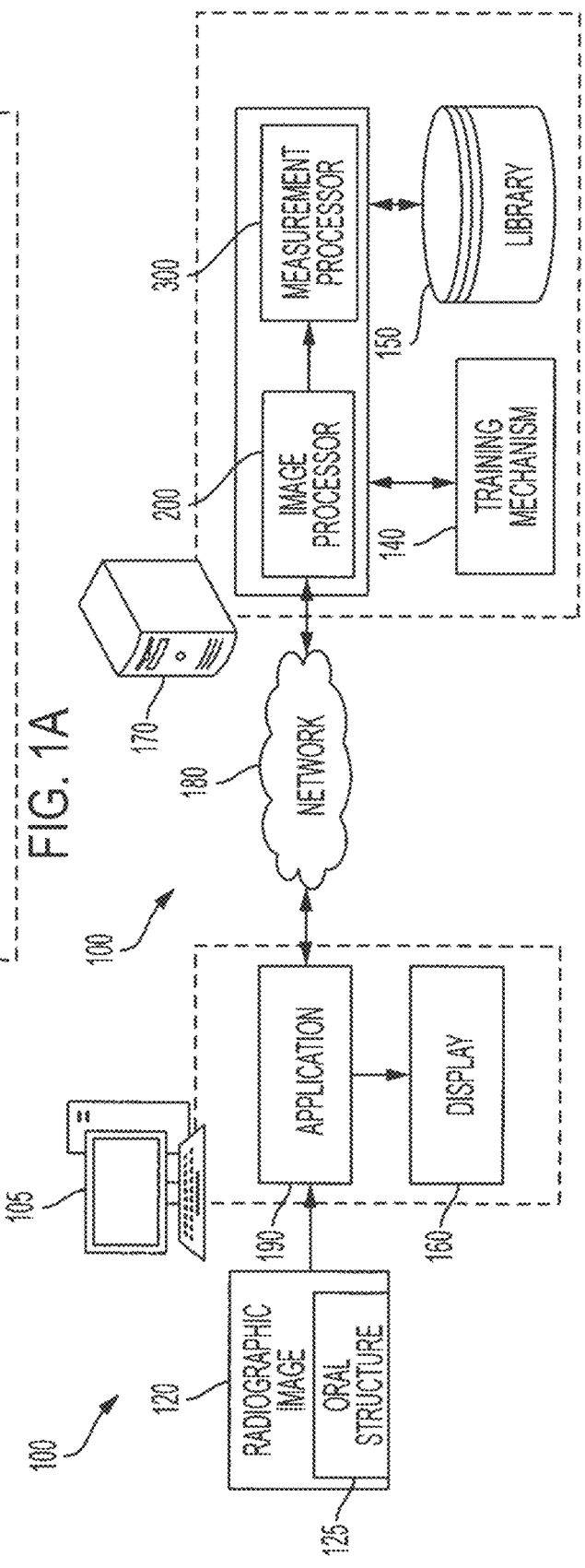

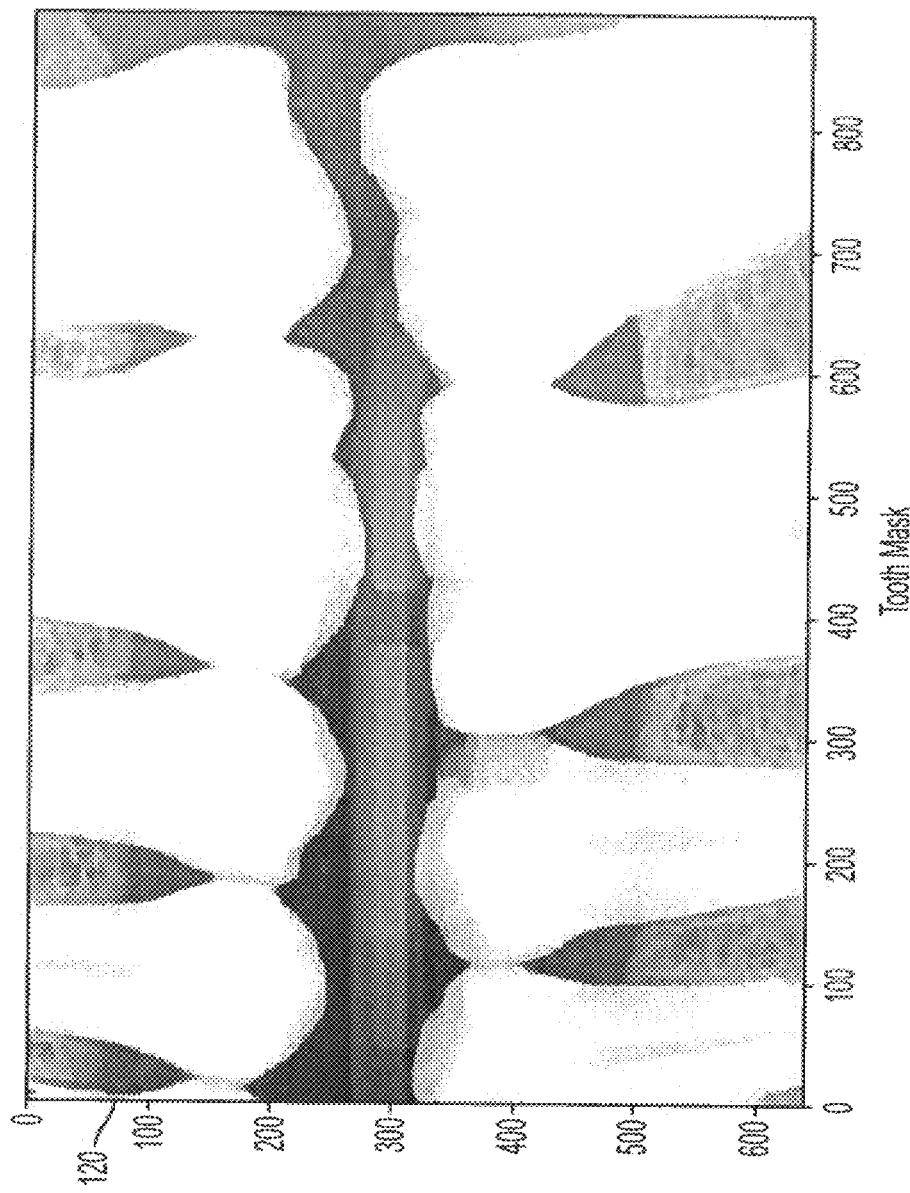

ESTIMATING MEASUREMENTS OF CRANIOFACIAL STRUCTURES IN DENTAL RADIOGRAPHS

TECHNICAL FIELD

This disclosure relates generally to image processing, and, more particularly, to a method of and system for estimating measurements of craniofacial structures by analyzing radiographic image data from different imaging modalities.

BACKGROUND

Accurately measuring oral structures present on a two-dimensional dental radiograph using currently available image processing methods is problematic. During the process of taking a dental radiograph, an x-ray sensor is positioned in a patient's mouth and an x-ray source is aligned with the sensor outside of the patient's mouth. The term craniofacial structure refers generally to the bones of the skull and face. The term 'oral structures' refers generally to natural teeth, restorations, implants, and any other structure that relates to craniofacial structures. Measurements of oral structures will typically include the relationship of the oral structure and craniofacial structure. When the x-ray source is activated, x-rays are sent toward the sensor, and any oral structures between the source and the sensor influence the resulting image. When an object is positioned upright and directly in the x-ray source's path, the object will be seen on the final image with minimal distortion. However, if the object's spatial orientation is changed in relation to the source and the sensor, the image of the object will be distorted. In controlled systems, the degree of distortion can be calculated if all angulations of the source, sensor, and object are known. In dentistry, however, the position of a patient's oral structures in relation to the sensor and the source can only be estimated.

To address these issues, external calibration objects have been imaged along with structures of interest to allow for image calibration. This type of calibration is only possible if the calibration object is present at the time that the radiographic image is captured.

Hence, there is a need for improved systems and methods to produce a more accurate approximation of absolute and relative measurements of oral structures featured within a radiographic image.

SUMMARY

In one general aspect, the instant application describes a data processing system having a processor and a memory in communication with the processor wherein the memory stores executable instructions that, when executed by the processor, cause the data processing system to perform multiple functions. The functions may include receiving a dental radiographic image that includes an oral structure, selecting a segmenter and an object detector, predicting masks and points of the oral structure using the segmenter and the object detector, providing the dental radiographic image and image metadata comprising the masks and points to a selector, selecting by the selector at least one measurement method of a set of measurement methods according to the dental radiographic image and the image metadata, calculating a sensor pixel to mm (millimeter) ratio using the measurement method, and calculating a calibrated measurement of the oral structure using the sensor pixel to mm ratio and the masks and points.

In yet another general aspect, the instant application describes a method for providing a calibrated measurement of an oral structure in a dental radiograph image. The method may include receiving a dental radiographic image that includes the oral structure, determining an image type of the dental radiographic image, based on the image type, selecting a segmenter and an object detector, predicting masks and points of the oral structure using the segmenter and the object detector, providing the dental radiographic image and image metadata comprising the masks and points to a selector, selecting by the selector at least one measurement method of a set of measurement methods according to the dental radiographic image and the image metadata, calculating a sensor pixel to mm (millimeter) ratio using the measurement method, and calculating a calibrated measurement of the oral structure using the sensor pixel to mm ratio and the masks and points.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The drawing figures depict one or more implementations in accord with the present teachings, by way of example only, not by way of limitation. In the figures, like reference numerals refer to the same or similar elements. Furthermore, it should be understood that the drawings are not necessarily to scale.

FIG. 1A-1B depict an example system and an alternative example service respectively upon which aspects of this disclosure may be implemented.

FIG. 4A-4E are examples of predicted masks and points that may be provided by the image processor.

DETAILED DESCRIPTION

Figure 2:
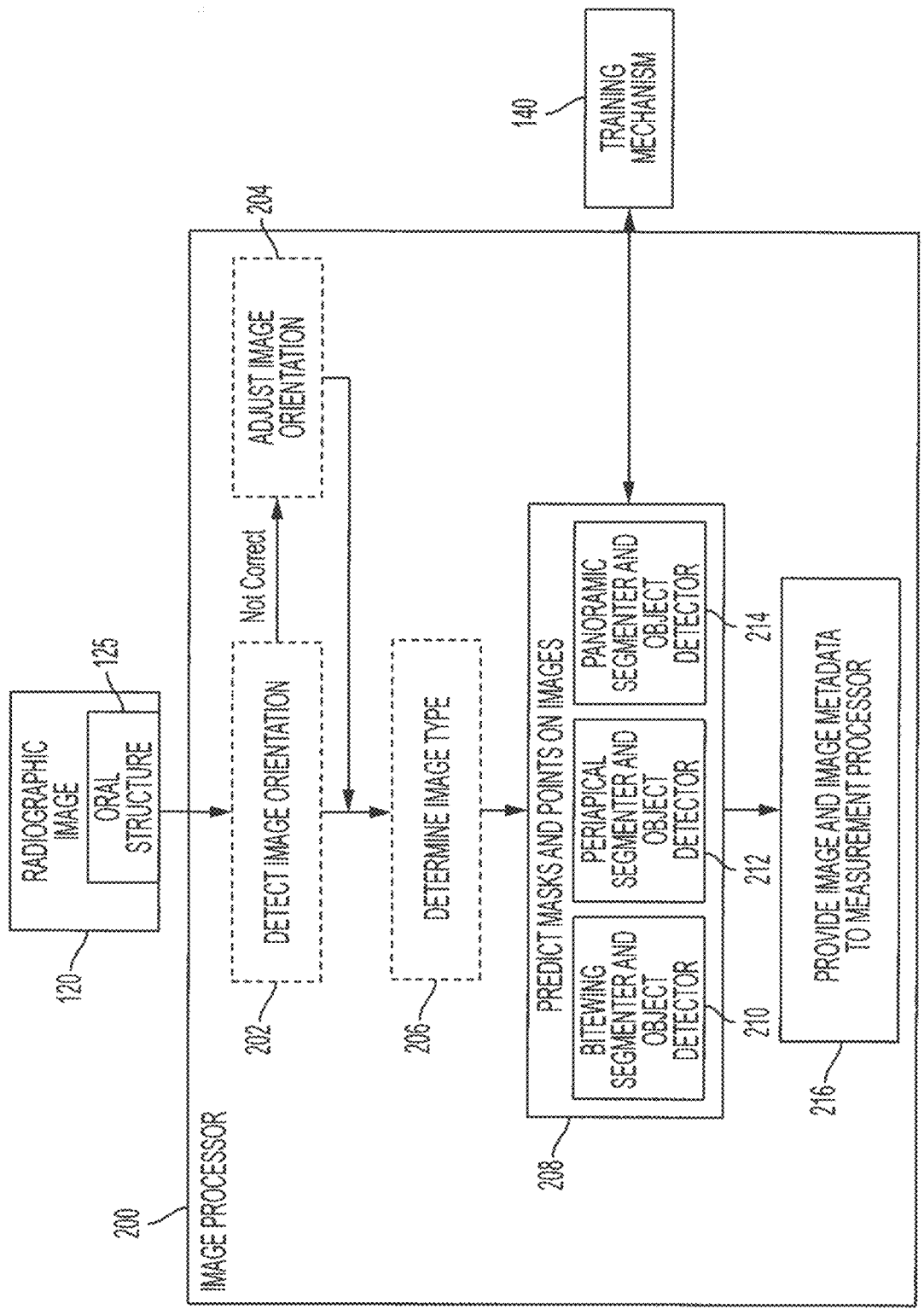
FIG. 2 is a flow diagram depicting an example method for an image processor for determining optionally image orientation and image type, predicting masks and points on images, and providing image and image metadata.

In the following detailed description, numerous specific details are set forth by way of examples in order to provide a thorough understanding of the relevant teachings. It will be apparent to persons of ordinary skill, upon reading this description, that various aspects can be practiced without such details. In other instances, well known methods, procedures, components, and/or circuitry have been described at a relatively high-level, without detail, in order to avoid unnecessarily obscuring aspects of the present teachings.

Accurately measuring oral structures present on a two-dimensional dental radiograph using currently available image processing methods is problematic. During the process of taking a dental radiograph, an x-ray sensor is positioned in a patient's mouth and an x-ray source is aligned with the sensor outside of the patient's mouth. When the x-ray source is activated, x-rays are sent toward the sensor, and any structures between the source and the sensor influence the resulting image. When an object is positioned upright and directly in the x-ray source's path, the object will be seen on the final image with minimal distortion. However, if the object's spatial orientation is changed in relation to the source and the sensor, the image of the object will be distorted. In controlled systems, the degree of distortion can be calculated if all angulations of the source, sensor, and object are known. In dentistry, however, the position of a patient's oral structures in relation to the sensor and the source can only be estimated.

To address these issues, external calibration objects have been imaged along with structures of interest to allow for image calibration. This type of calibration is only possible if the calibration object is present at the time that the radiographic image is captured.

The proposed invention uses a patient's unique anatomical oral structures as calibration objects to make calibrated measurements without the need for an external calibration object. Additionally, the invention can calculate the angle between a patient's oral structures and the x-ray source and sensor, when 3-dimensional measurements of structures featured in the produced radiographic images are available.

As will be understood by persons of skill in the art upon reading this disclosure, benefits and advantages provided by such implementations can include, but are not limited to, a technical solution to the technical problems of using a patient's unique anatomical oral structures as calibration objects to make calibrated measurements without the need for an external calibration object. Technical solutions and implementations provided herein optimize the process of obtaining calibrated measurements of oral structures featured in 2D dental radiographs. The benefits provided by these technology-based solutions yield more user-friendly applications, increased accuracy and increased system and user efficiency.

As a general matter, the methods and systems described herein may include, or otherwise make use of, a machine-trained model to identify contents related to a text. Machine learning (ML) generally involves various algorithms that a computer can automatically learn over time. The foundation of these algorithms is generally built on mathematics and statistics that can be employed to predict events, classify entities, diagnose problems, and model function approximations. As an example, a system can be trained using data generated by a ML model in order to identify patterns in dental radiographs as applied to image processing. Such determinations may be made following the accumulation, review, and/or analysis of user data from a large number of users over time as well as individual patient data, that may be configured to provide the ML algorithm (MLA) with an initial or ongoing training set. In addition, in some implementations, a user device can be configured to transmit data captured locally during use of relevant application(s) to the cloud or the local ML program and provide supplemental training data that can serve to fine-tune or increase the effectiveness of the MLA. The supplemental data can also be used to facilitate identification of contents and/or to increase the training set for future application versions or updates to the current application.

In different implementations, a training system may be used that includes an initial ML model (which may be referred to as an "ML model trainer") configured to generate a subsequent trained ML model from training data obtained from a training data repository or from device-generated data. The generation of this ML model may be referred to as "training" or "learning." The training system may include and/or have access to substantial computation resources for training, such as a cloud, including many computer server systems adapted for machine learning training. In some implementations, the ML model trainer is configured to automatically generate multiple different ML models from the same or similar training data for comparison. For example, different underlying ML algorithms may be trained, such as, but not limited to, decision trees, random decision forests, neural networks, deep learning (for example, convolutional neural networks), support vector machines, regression (for example, support vector regression, Bayesian linear regression, or Gaussian process regression). As another example, size or complexity of a model may be varied between different ML models, such as a maximum depth for decision trees, or a number and/or size of hidden layers in a convolutional neural network. As another example, different training approaches may be used for training different ML models, such as, but not limited to, selection of training, validation, and test sets of training data, ordering and/or weighting of training data items, or numbers of training iterations. One or more of the resulting multiple trained ML models may be selected based on factors such as, but not limited to, accuracy, computational efficiency, and/or power efficiency. In some implementations, a single trained ML model may be produced.

The training data may be continually updated, and one or more of the models used by the system can be revised or regenerated to reflect the updates to the training data. Over time, the training system (whether stored remotely, locally, or both) can be configured to receive and accumulate more and more training data items, thereby increasing the amount and variety of training data available for ML model training, resulting in increased accuracy, effectiveness, and robustness of trained ML models.

FIG. 1A illustrates an example system 100 upon which aspects of this disclosure may be implemented. The system 100 may include a computer 105 executing software that implements an image processor 200 which is coupled to receive a radiographic image 120 containing an oral structure 125 that could comprise a natural tooth, an implant, a restoration, etc. that further relates to craniofacial structures such as bone. The image processor 200 provides image metadata to a measurement processor 300 which in turn provides a calibrated measurement based on the image metadata and data from a library 150 that may include an X-ray sensor database, an implant database, a population based anatomical averages database, and a patient specific database, as shown in greater detail in subsequent paragraphs. A training mechanism 140 provides a machine-learning based training mechanism as mentioned above for training aspects of the image processor 200 for better predicting masks and points of the oral structure 125. A display 160 enables the display of a graphical user interface (GUI) for displaying the calibrated measurement.

FIG. 1B illustrates an alternative embodiment of the example system 100 upon which aspects of this disclosure may be implemented as a web service including the computer 105 operating as a client device for executing client application 190 software that is coupled to receive a radiographic image 120 containing an oral structure 125 that could comprise a natural tooth, an implant, a restoration, etc. A server 170 runs a server-side application such as In a cloud service executing software that communicates with the application 190 via a network 180 to receive the radiographic image 120. Server 170 executes software for implementing the image processor 200 that provides image metadata to the measurement processor 300 which in turn provides a calibrated measurement based on the image metadata and data from the library 150 that may include an X-ray sensor database, an implant database, a population based anatomical averages database, and a patient specific database. The training mechanism 140 provides a machine-learning based training mechanism for training aspects of the image processor for better predicting masks and points of the oral structure 125. The display 160 as part of the application 190 enables the display of a graphical user interface (GUI) for displaying the calibrated measurement received from the server 170.

Figure 3A:
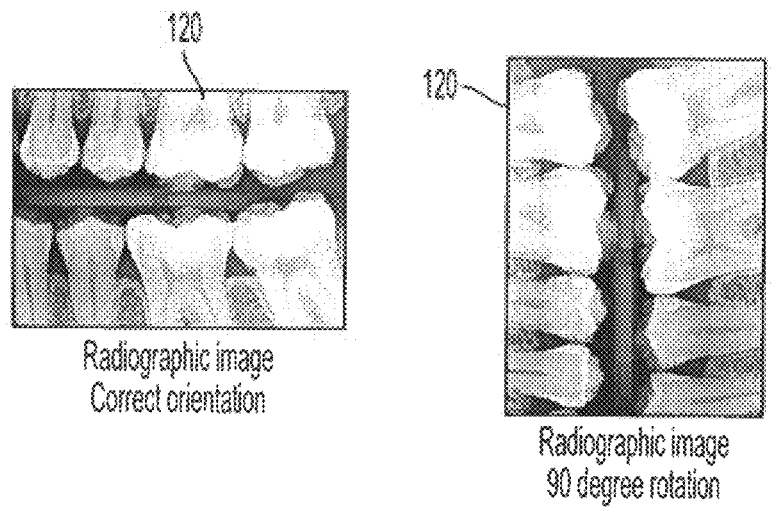
FIG. 3A-3B are examples of radiographic image types detected by the image processor.
Figure 3B:
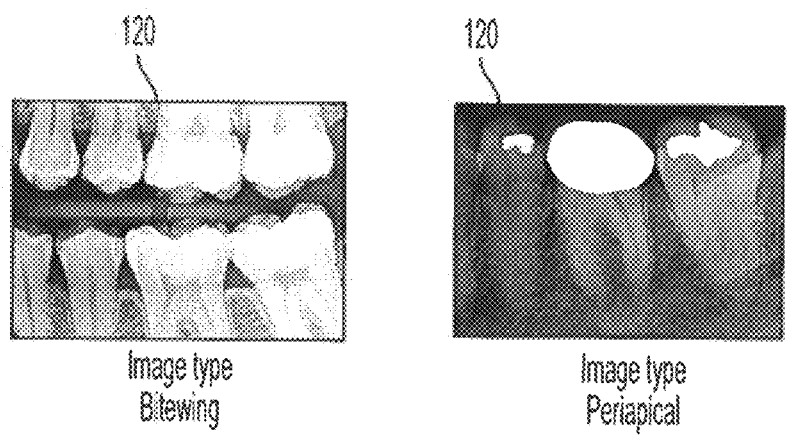
Figure 4A:
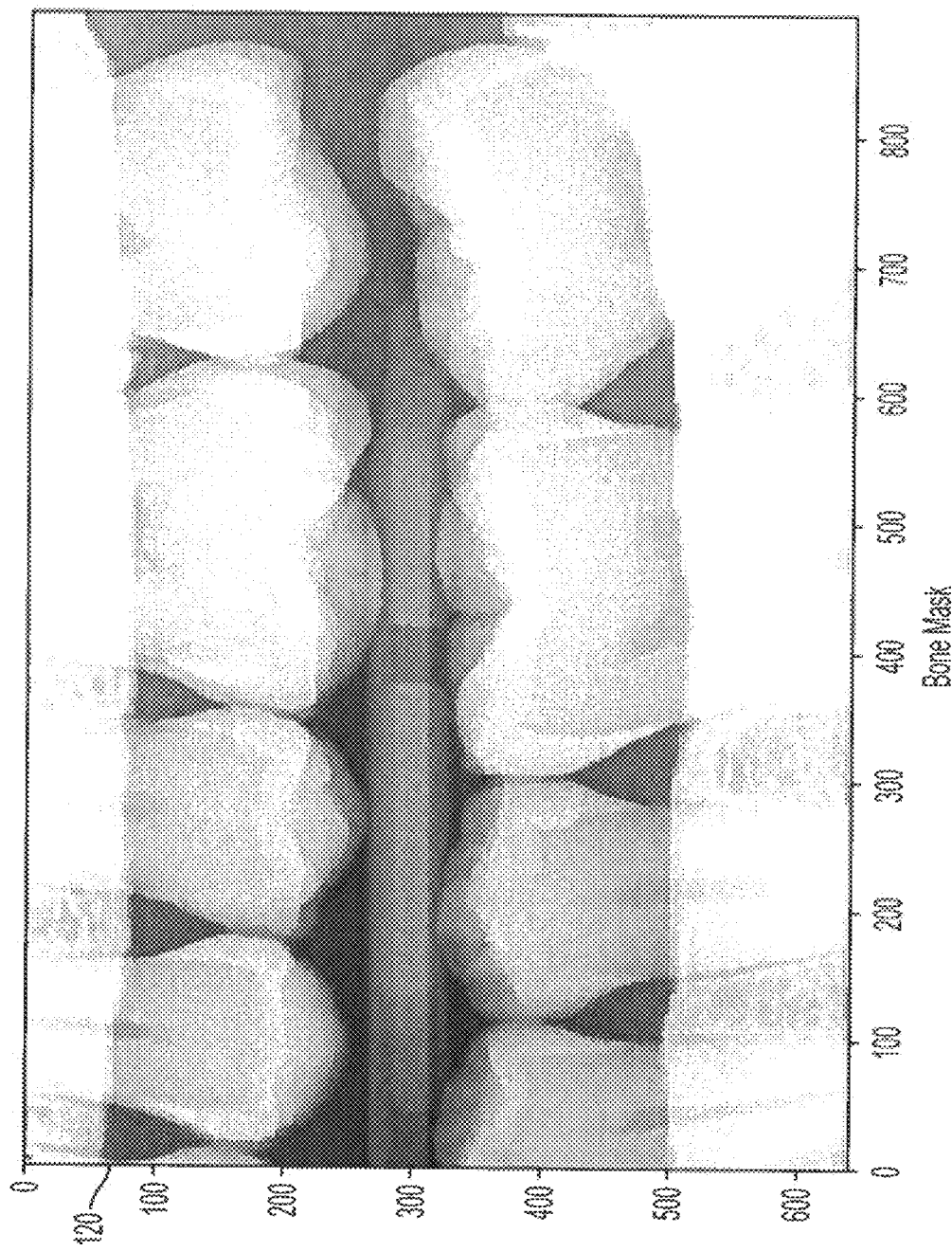
Figure 4B:
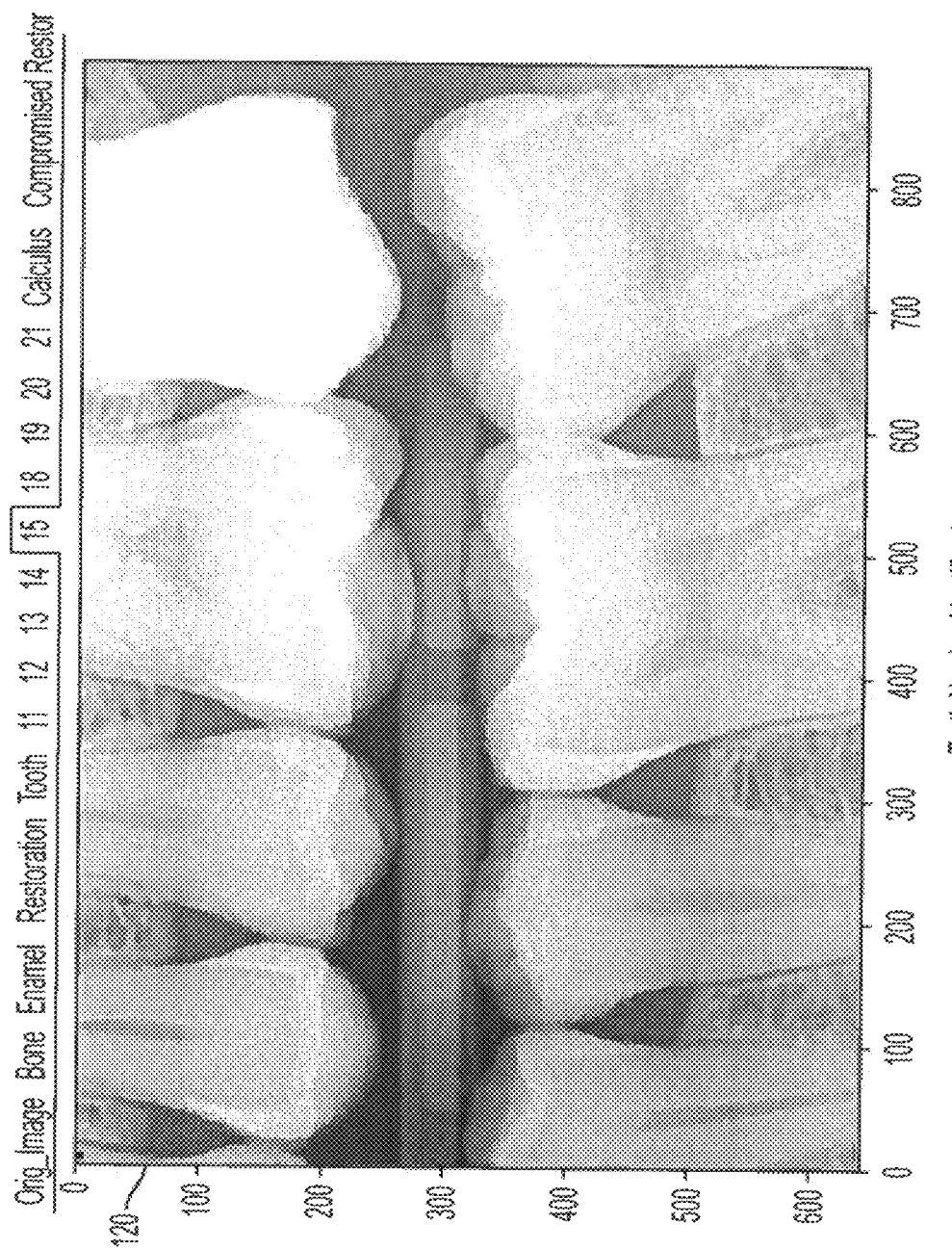
Figure 4D:
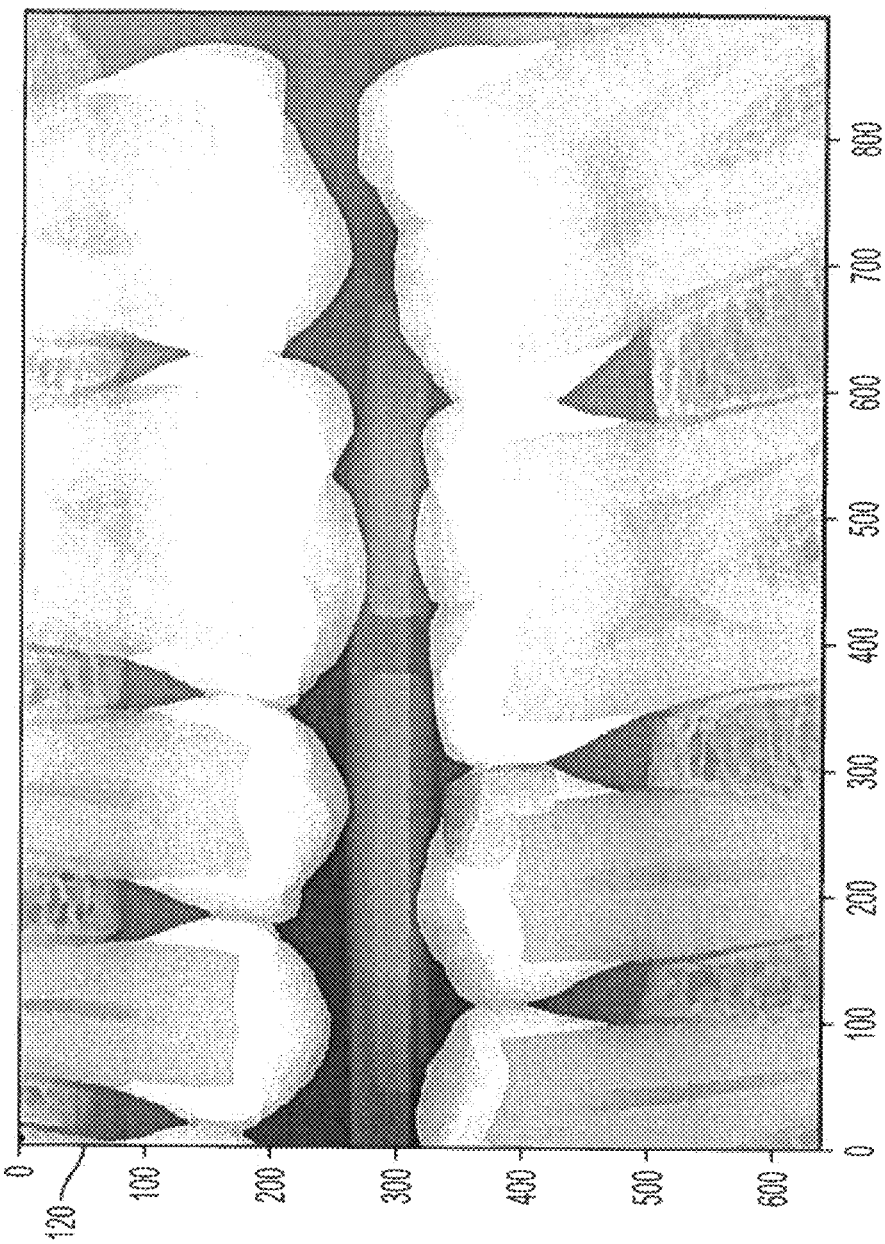
Figure 4E:
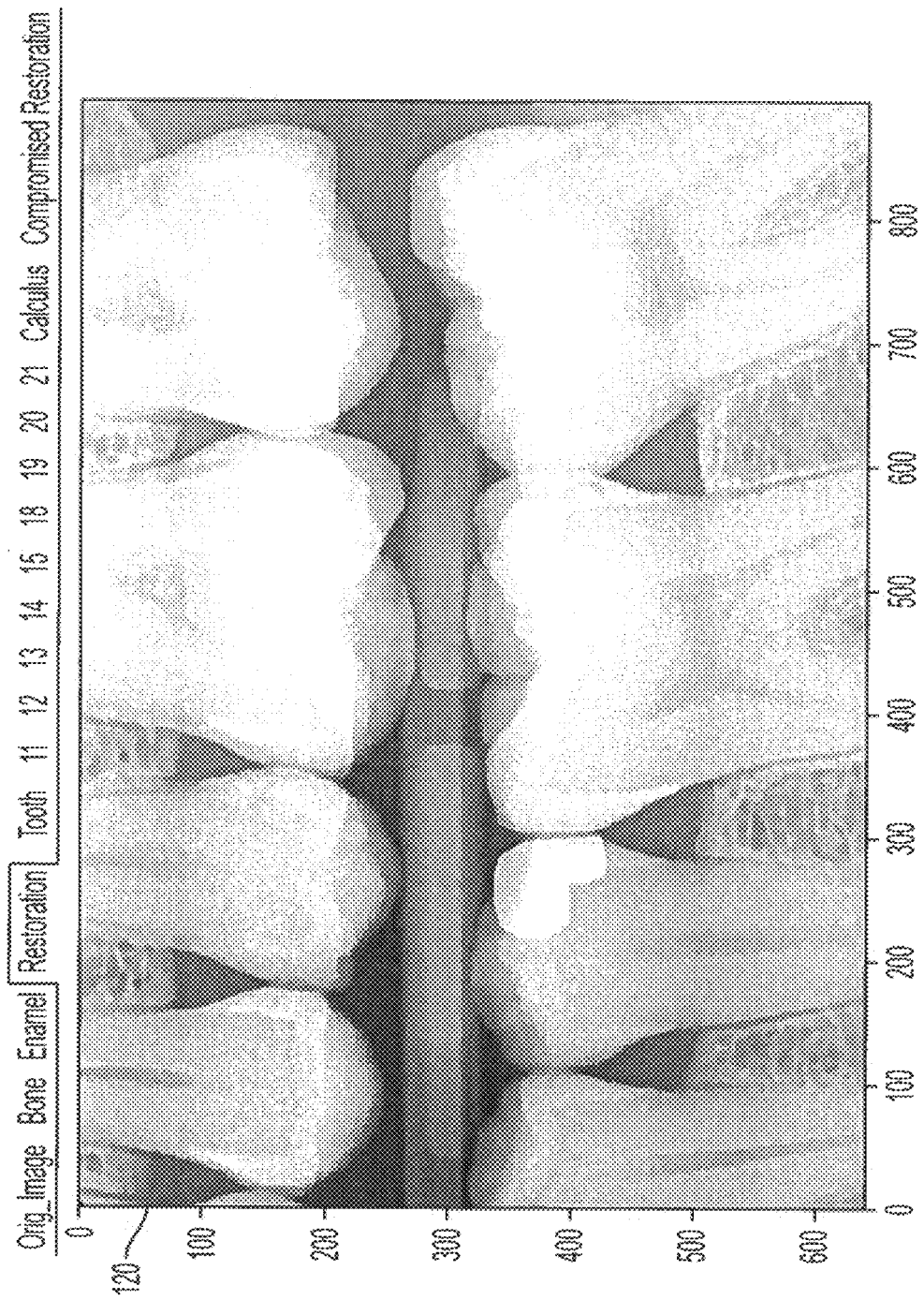

FIG. 2 depicts the operation of the image processor 200 that receives the radiographic image 120 containing oral structure 125. An initial transformation step that converts images to a standard format such as JPEG or PNG may be required. At step 202, the image orientation is optionally detected, if the image orientation is not correct, the orientation is optionally adjusted at step 204. Steps 202-206 may optionally be done as advantageous in the image processor 200. FIG. 3A depicts the radiographic image 120 at a correct orientation and at a 90-degree rotation that would require adjustment. At step 206, an image type for the radiographic image 120 is optionally determined. FIG. 36 depicts the radiographic image 120 with example image types that include bitewing and periapical, among others. Referring back to FIG. 2, in step 208, masks and points on the radiographic image 120 are predicted by a segmenter and object detector. Depending on the image type as determined in step 206, appropriate pairs of segmenters and object detectors are chosen from a set of segmenters and object detectors 210-214, including selecting among Bitewing Segmenter and Object Detector 210, Periapical Segmenter and Object Detector 212, and Panoramic Segmenter and Object Detector 214 in order to provide the desired masks and points prediction. The Bitewing Segmenter and Object Detector 210, Periapical Segmenter and Object Detector 212, and Panoramic Segmenter and Object Detector 214 may use different Deep Learning (DL) based ML models are used for prediction. For example, bitewing specialized anatomy training models may desirably be used better prediction of bitewing images. The DL model predicts masks for many labels such as tooth number, general tooth area, bone, enamel, restorations such as crown, filling/inlay, onlay, bridge, implants etc. The DL model itself is an amalgam of several semantic segmentation and object detection models. The best model identified with the help of metrics such as Intersection over Union (IoU) and bone level (distance between Cemento Enamel Junction (CEJ) and bone point) against a test set is chosen for the particular label. Further, the model also directly predicts the CEJ, and alveolar bone crest (hereafter called bone) points per tooth number. The model provides two ways of getting CEJ and bone points, which can be used to improve the confidence of the measurements. The masks and points are both in terms of pixel measurements. It will be understood that any number of different image types coupled with an appropriate segmenter and object detector may be employed as desirable. The training mechanism 140 provides for training the ML models for the Bitewing Segmenter and Object Detector 210, the Periapical Segmenter and Object Detector 212, and the Panoramic Segmenter and Object Detector 214 in order to provide the mask and points prediction.

FIG. 4A-4E depict various non-limiting examples of the masks and points that may be handled by the Segmenter and Object Detectors 210-214 for the oral structures 125 in the radiographic image 120, including the Bone Mask, Tooth Number Identification, Tooth Mask, Enamel Identification, and Restorations. In step 216, the radiographic image 120 and image metadata comprising the image type and associated masks and points are provided to the measurement processor 300.

Figure 5:
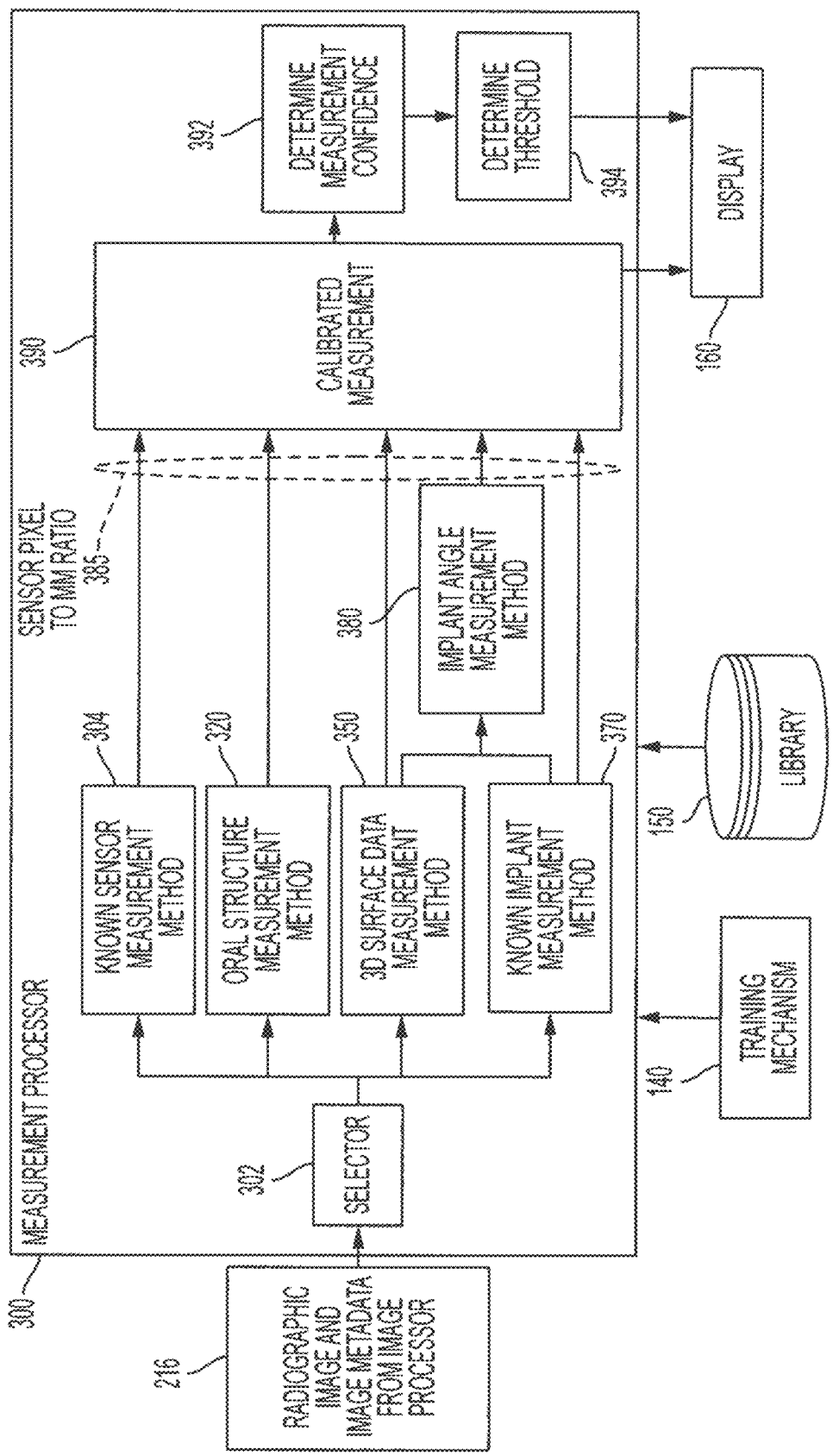
FIG. 5 is a flow diagram depicting a measurement processor that determines a sensor pixel to mm (millimeter) ratio by selecting from at least one method, and further provides a calibrated measurement and a threshold.

FIG. 5 depicts the operation of the measurement processor 300 which receives the radiographic image 120 and the image metadata 216 from the image processor 200. The radiographic image 120 and image metadata 216 provide measurements in terms of pixels that require calibration via selection of one or more of methods 304, 320, 350, 370, and 380 by a selector 302 to obtain a sensor pixel to mm (millimeter) ratio 385. Selector 302 may operate according to a set of rules that determine which of the methods 304, 320, 350, 370, and 380 are selected. If the image metadata includes a known sensor type or a sensor type that can be determined, then Known Sensor Measurement Method 304 is selected. If the image metadata does not include a known sensor type or the sensor type that cannot be determined, then Oral Structure Measurement Method 320 is selected. If 3D surface data measurement data is available, such as from library 150, then 3D Surface Data Measurement Method 350 is selected. If the image metadata includes a known implant as part of the image metadata, then Known Implant Measurement Method 370 is selected. Further, if both 3D surface data measurements are available along with known implant measurement data from methods 350 and 370, then implant Angle Measurement Method 380 can also be chosen to obtain the most accurate measurement. Based on radiographic image 120 and image metadata 216 from image processor 200, in combination with calibration measurement 390, the measurement confidence level 392 can be determined along with a threshold 394. The calibrated measurement 390 along with threshold 394 can subsequently be provided to display 160 as part of a user interface. The detailed operation of methods 304, 320, 350, 370 and 380 will be explained in further detail below in FIGS. 6-12.

An alternative embodiment of selector 302 includes a machine learning implementation in which any of various combinations of the measurement methods 304, 320, 350, 370, and 380 can be selected according to optimization techniques that provide for calibrated measurement may be optimized for measurement speed, accuracy, or threshold as desired using ML as provided by the training mechanism 140. The machine learning model may be based on specific patient characteristics as well as crowdsourced methods that provide for overall measurement techniques.

Figure 6:
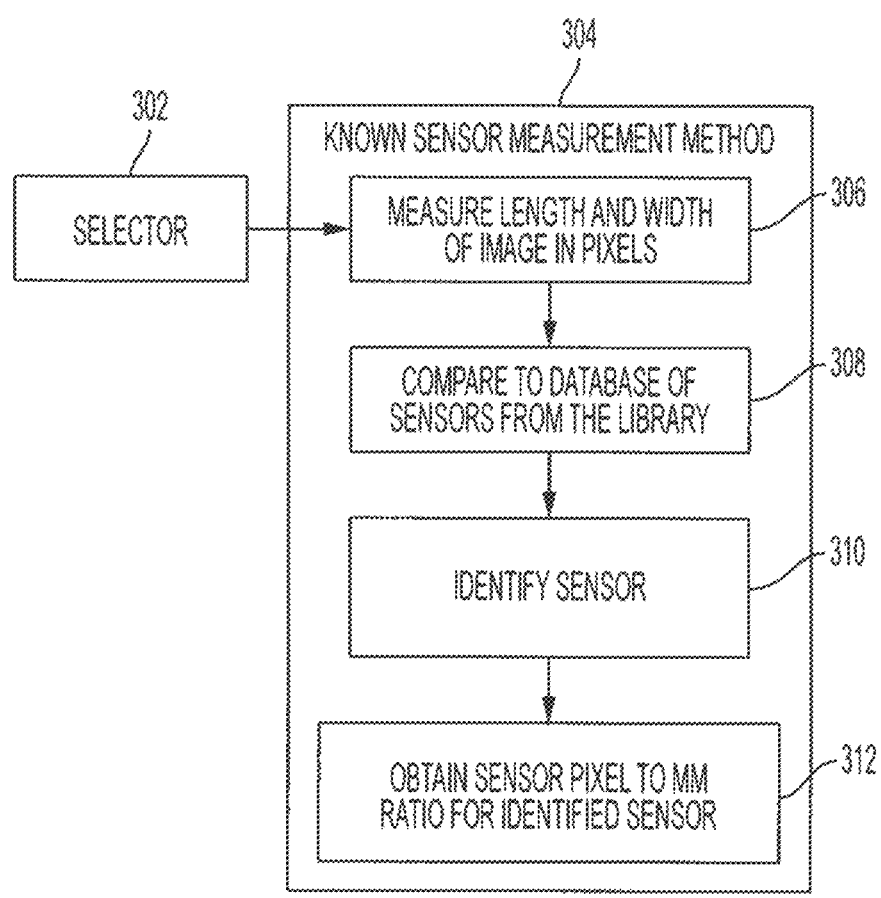
FIG. 6 is a flow diagram depicting a first measurement method in the measurement processor of FIG. 5 for obtaining sensor pixel to mm ratio when the sensor can be determined.

FIG. 6 depicts Known Sensor Measurement Method 304 as selected by selector 302. Given that the radiographic image metadata includes a known sensor type or a sensor type that can be determined, information contained in the library 150 may include known sensor types that further include length and width measurements of image 306 in pixels in step 306. In step 308, the length and width are compared to a database of sensors from the library 150 and from that comparison, sensor 310 is identified. Once the sensor 312 has been identified, the sensor pixel the sensor pixel to mm (millimeter) ratio for the sensor 312 can be provided according to the database of sensors from the library 308.

Figure 7:
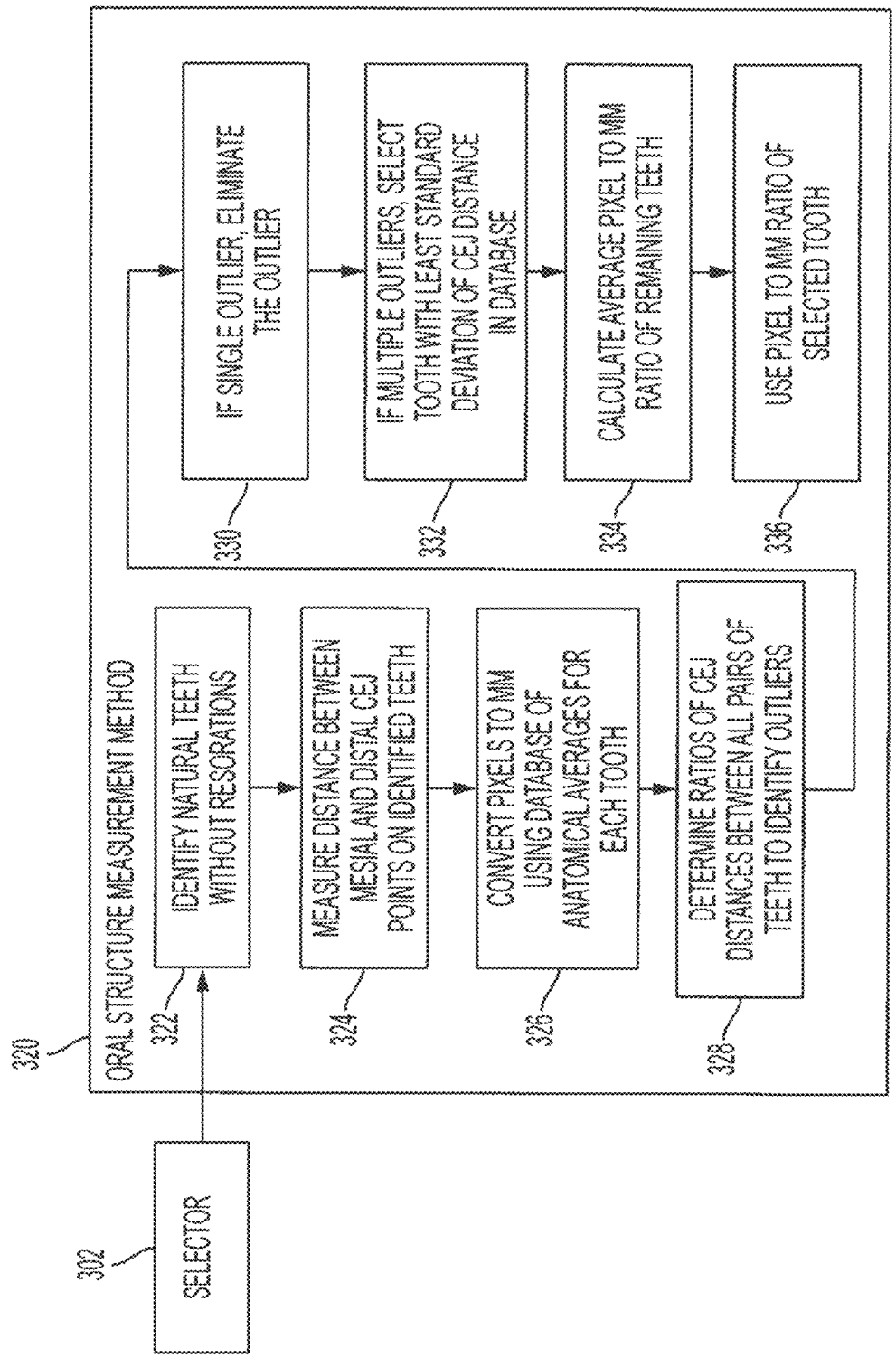
FIG. 7 is a flow diagram depicting a second example method in the measurement processor of FIG. 5 that determines a sensor pixel to mm (millimeter) ratio using radiographic images of natural teeth when an image sensor cannot be determined.

FIG. 7 depicts Oral Structure Measurement Method 320 as selected by selector 302. Given that the radiographic image metadata does not include a known sensor type or a sensor type that can be determined Oral Structure Measurement Method 320 is selected as an alternative to obtain calibrated measurements using oral structures in the radiographic image. In step 322, natural teeth without restorations are identified as an oral structure. In step 324, a distance is measured between mesial and distal CEJ points on the identified teeth. In step 326, selected conversions of pixels to millimeter using a database of anatomical averages for each tooth as obtained from library 150 are made. In step 328, ratios of CEJ distances between all pairs of teeth to identify outliers are determined. In Step 330, if there is a single outlier, then that outlier may be eliminated. In step 332, if there are multiple outliers select a tooth with the least standard deviation of CEJ distance in the database. In step 334 an average pixel to millimeter ratio of remaining teeth are calculated. In step 336 a pixel to millimeter ratio of the selected tooth is made.

The process of identifying outliers and eliminating them may be done in alternative and more sophisticated ways, for example, using Kalman filtering to eliminate sources of error to the extent possible. An alternative embodiment for steps 330 through 334 may include the use machine learning methods which would provide a more flexible method of choosing which tooth and which measurement to obtain the pixel to millimeter ratio that includes a known sensor type or a sensor type that can be determined. For example, decisions based on trained ML models may identify a particular tooth or a particular set of measurements will likely provide optimal results based on experience with a particular patient or a particular set of patients to obtain the most reliable measurement in the radiographic image 125.

Figure 8A:
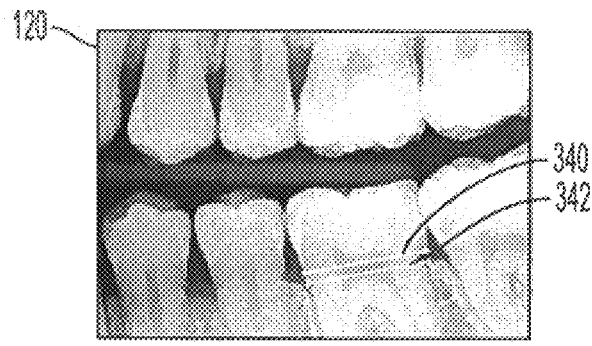
FIG. 8A-8B are examples of measurements performed on radiographic images of natural teeth according to the method of FIG. 7.
Figure 8B:
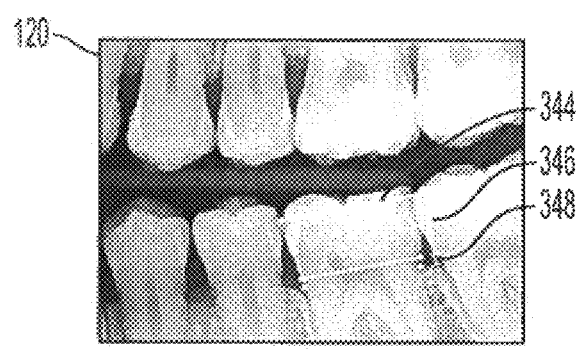

FIGS. 8A and 8B illustrate the measurements performed in step 324 of the image processor 200 operating on the radiographic image 120 and oral structure 125 to identify the appropriate points necessary for measurements of the oral structure 125. The outer border of the dental crowns is traced using at least one of the Segmenter and Object Detectors 210-212 according to the image type. A minimum distance of each pixel of the outer border of the occlusal surface from the CEJ to CE line is calculated and an occlusal surface line 344 parallel to the CE to CEJ point line 340 is generated at the average minimum distance of all pixels included within the occlusal surface. An CEJ-occlusal plane line distance 346 between the occlusal surface line 344 and the CEJ to CE line 340 is measured in pixels. A ratio between the CEJ-occlusal plane line distance 346 and a CE-boney crest distance 348 is calculated and compared with reference data from the library 150 to determine if local bone loss is present above a determined bone loss threshold.

Figure 9:
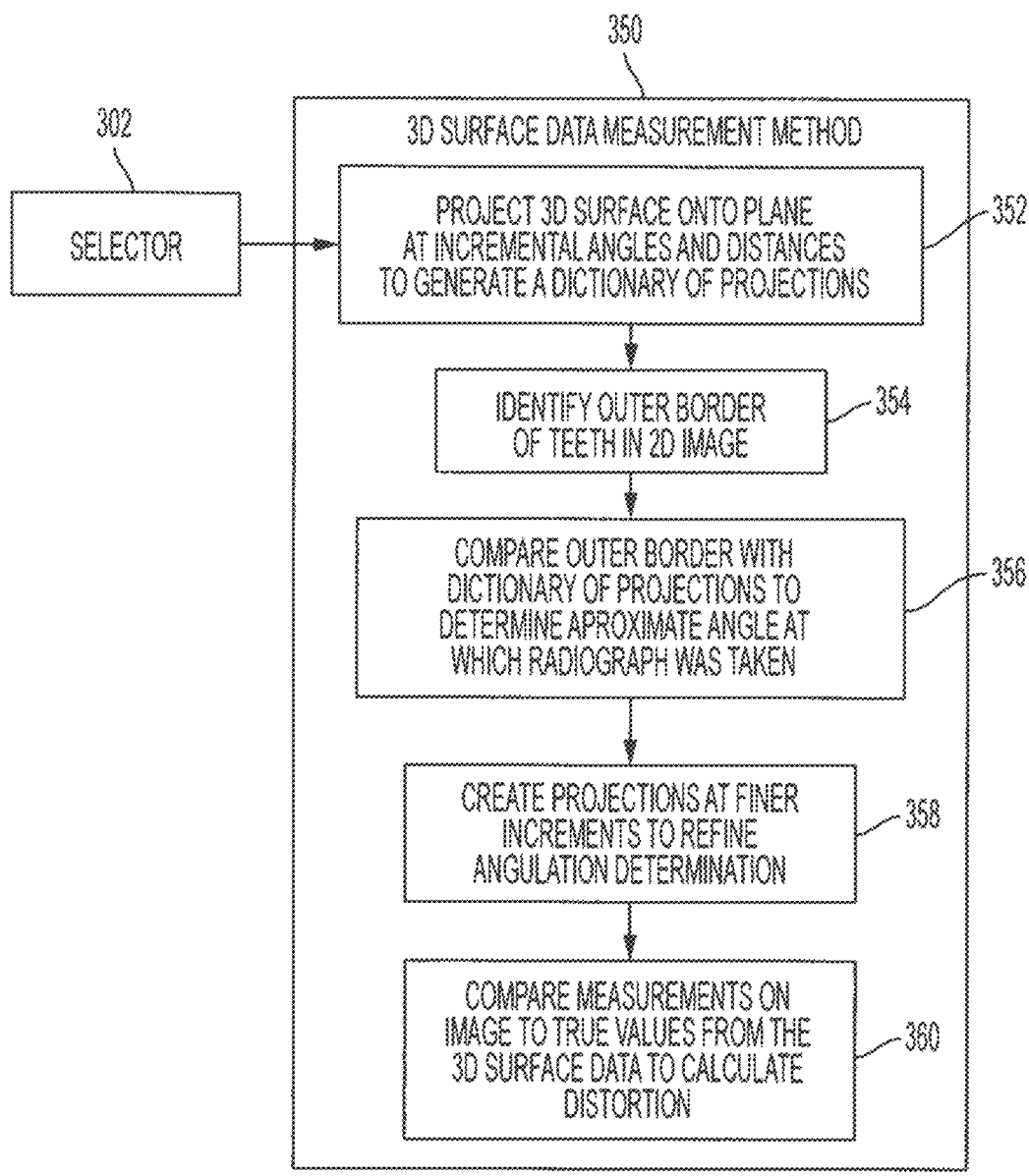
FIG. 9 is a flow diagram depicting a third example method in the measurement processor of FIG. 5 that determines a sensor pixel to mm (millimeter) ratio using radiographic images of natural teeth when an image sensor cannot be determined.

FIG. 9 depicts 3D Surface Data Measurement Method 350 as selected by selector 302. Surface Data Measurement Method 350 is used when sensor can or cannot be determined. If the sensor information is present the 3D surface data provides increases accuracy of measurement by accounting for image angulations. If the sensor information is not present, the 3D surface data may be used to provide mm to pixel ratio.

Data from 3D dental imaging, such as an optical surface scan and/or cone beam computed tomography, is used to generate a dictionary of 2D projections of the oral structures projected onto a plane at incremental distances and from incremental angles. A computational minimization problem will be utilized to arrive at final solution. A 2D (two dimensional) radiographic image is analyzed to determine the outer border of craniofacial structures of interest within the image, and the library of two dimensional projections is searched to determine a match between the radiographic image and a two dimensional projection from the library. The matched images can then be used to determine the angulation at which the original 20 radiographic image was taken. 30 structures can be used to calculate angulation of the x-ray source compared with the imaged structures include dental implants, dental restorations, and dental hard tissue structures (e.g. teeth and bone). When the angulation of the imaged oral structure 125 is known, the total distortion of the image can be calculated, and for distances measured on dental radiographs to be calibrated.

Figure 10:
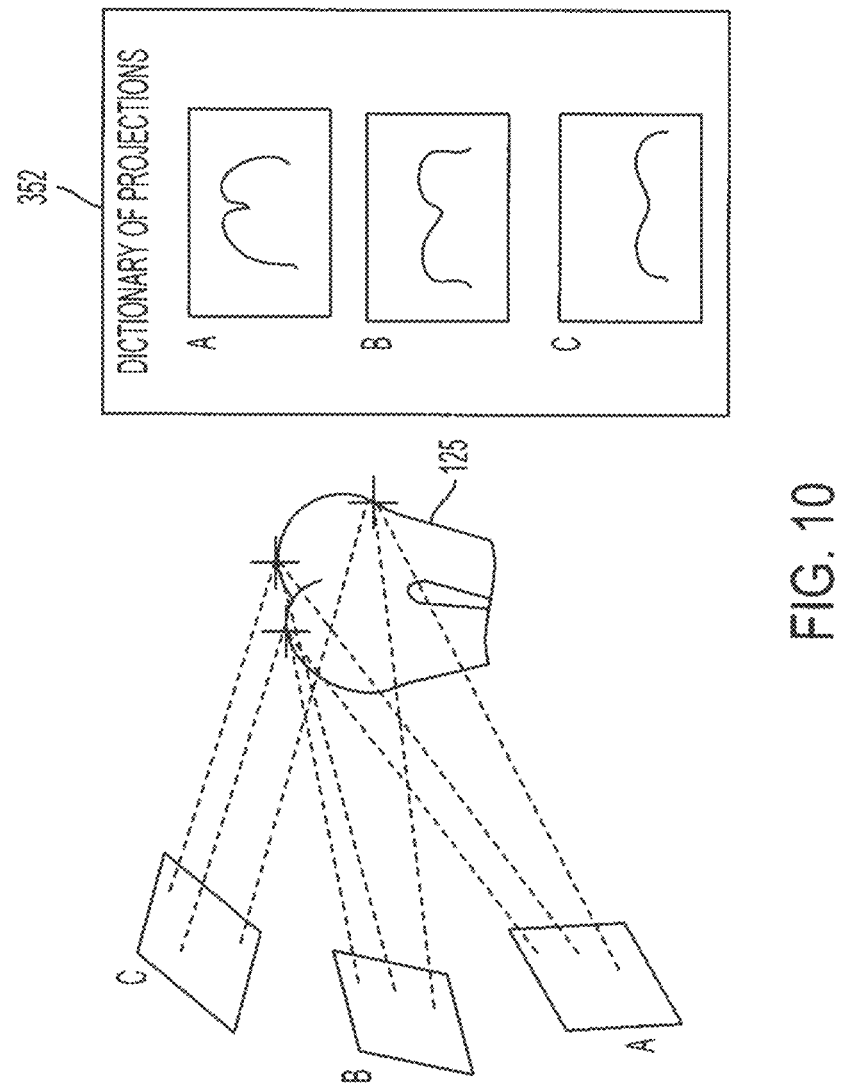
FIG. 10 illustrates the projection of a 3D (three-dimensional) surface onto a plane at incremental angles to generate a dictionary of projections.

FIG. 10 depicts a dictionary of projections 352 that can be generated by projecting a 3D surface, in this case the oral structure 125, onto a plane at incremental angles as shown across angles A, B, and C. Any number of possible angles and projections may be chosen to create the dictionary of projections 352 to obtain a desired level of precision. The Dictionary of Projections 352 may be stored in and subsequently retrieved from the library 150 in a manner offline to the current measurement being performed by method 350.

Potential applications for calibrated distance measurements in dentistry may include, but are not limited to: measuring root canal length during endodontic procedures, measuring root canal length and length of canal preparation during dental post placement procedures, measuring vertical and horizontal dimension of bone in prospective implant placement sites, determining vertical level of alveolar bone in relation to adjacent structures (e.g. teeth) to monitor periodontal disease progression, and determining distance between dental restorations and the underlying alveolar bone, measuring distance between inferior alveolar nerve and adjacent structures, objects or osteotomy sites, measuring distance between maxillary sinus floor and adjacent structures, objects or osteotomy sites, and determining angulation of implants compared to adjacent teeth and structures.

Referring back to FIG. 9, in step 354, the outer border of teeth, corresponding to the oral structure 125 in the radiographic image 120, are identified. In step 356, the outer border is compared with the Dictionary of Projections 352 to determine the approximate angle at which the radiographic image 120 was taken. In step 358, projections may be created or retrieved from the library 150 at increasingly finer increments as desired to refine an angulation determination. In step 360, measurements from the radiographic image 120 and oral structure 125 are compared with true measurement values from the Dictionary of Projections 352 to calculate a distortion value related to the approximate angle that can be used to determine the pixel to millimeter ratio.

Figure 11:
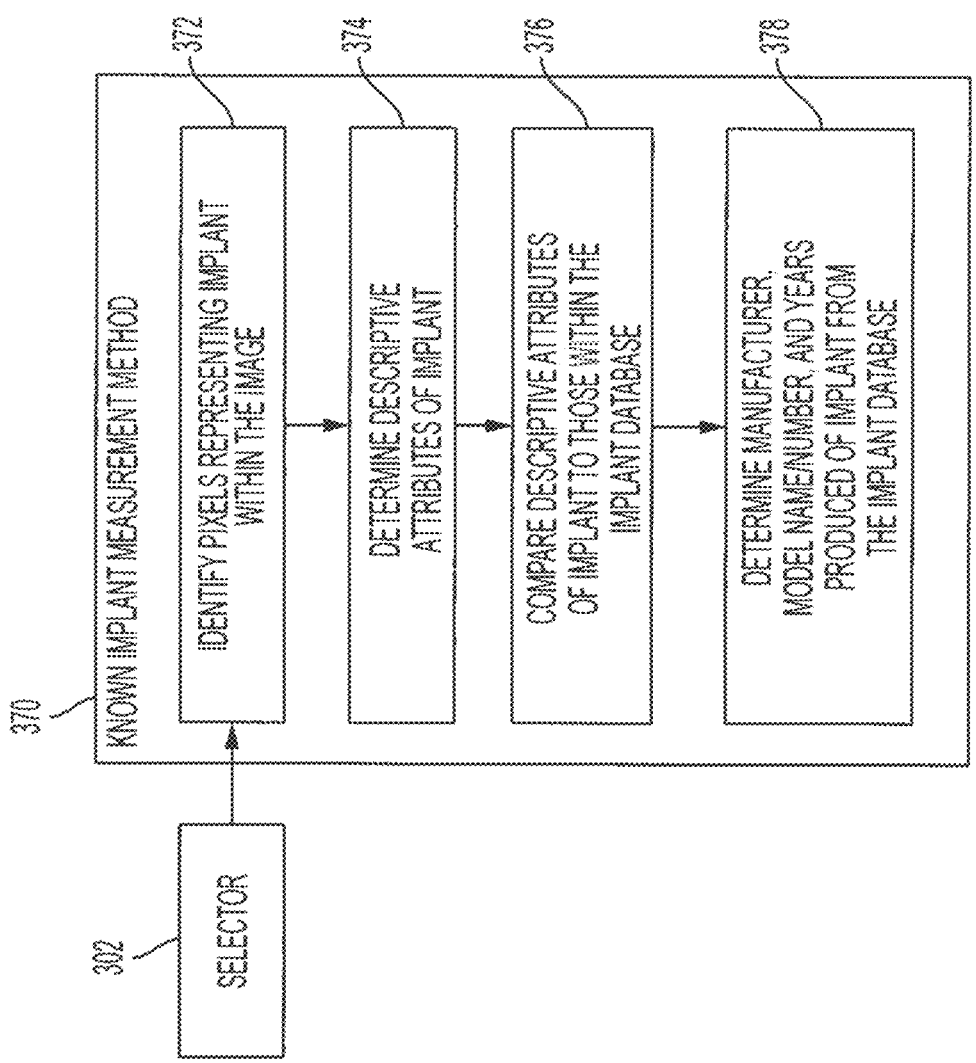
FIG. 11 is a flow diagram depicting a fourth example method in the measurement processor of FIG. 5 that determines a sensor pixel to mm (millimeter) ratio by identifying an implant from an implant database when an image sensor cannot be determined.

FIG. 11 depicts a Known Implant Measurement Method 370 as selected by selector 302. In step 372, pixels representing a dental implant within the radiographic image 120 as the oral structure 125 image are identified. In step 374, descriptive attributes of the dental implant are determined. In step 376, the descriptive attributes of the dental implant are compared to those within a dental implant database from library 150. In step 378, analyzes pixels representing the implant(s) for descriptive attributes of the implant(s) are analyzed, including for example: Type of implant interface, Flange shape, Presence or absence collar and shape of collar, Presence or absence of micro-threading, Presence or absence of implant taper and location of taper, Presence or absence of threads and number of threads, Presence or absence of midbody grooves, Shape of implant apex, Presence or absence of open implant apex, Presence or absence of holes and shape of holes present, Presence or absence of an apical implant chamber, and Presence or absence of apical grooves. A list of identified attributes and identifies implants with identical attributes stored within a database of previously classified implant models retrieved from library 150. Information retrieved about the implant may include the Manufacturer, Model name and/or number, Years during which the reported implant model was produced by manufacturer as obtained from the implant database. Given the detailed geometric information available about the dental implant, the pixel to millimeter ratio 385 can then be determined.

Figure 12:
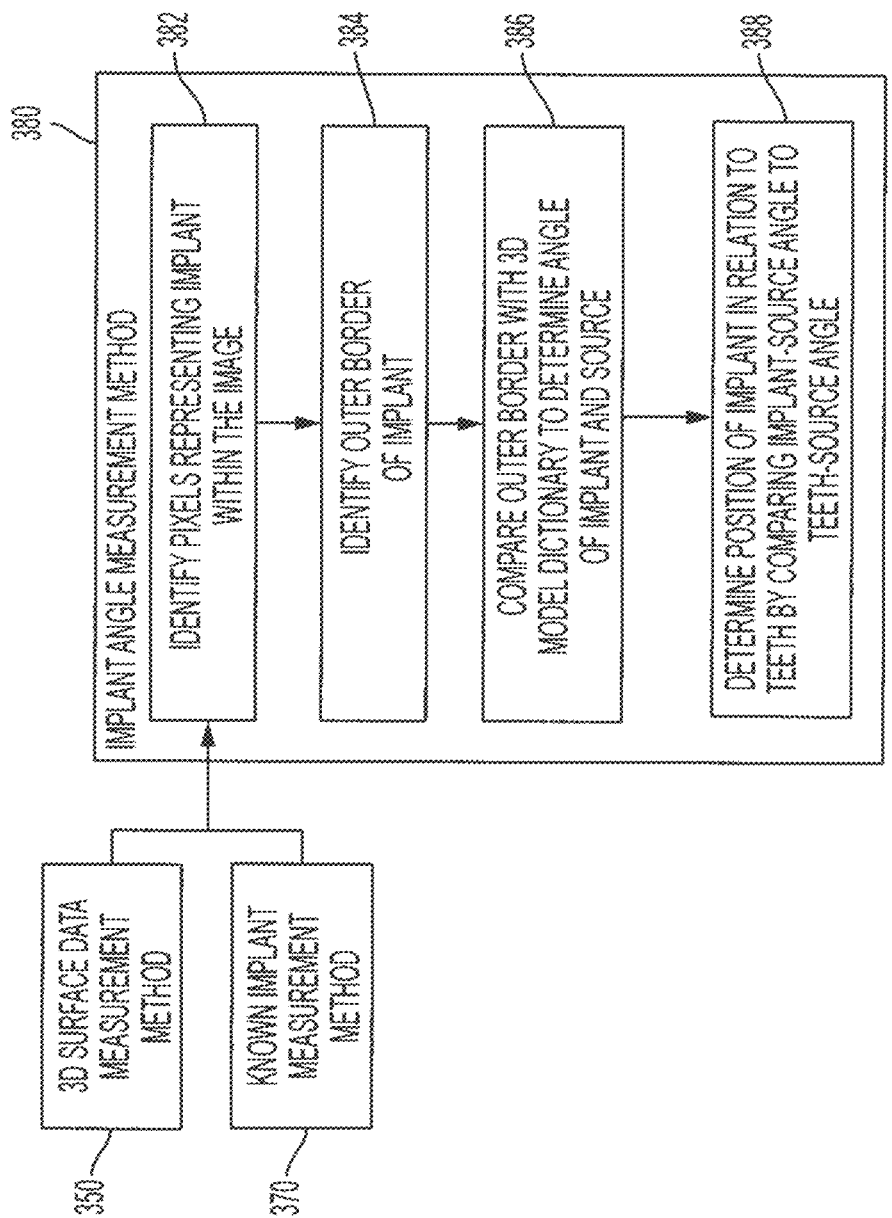
FIG. 12 is a flow diagram depicting a fifth example method in the measurement processor of FIG. 5 that determines a sensor pixel to mm (millimeter) ratio using the metadata from the third and fourth methods.

FIG. 12 depicts the implant Angle Measurement Method 380 as selected by selector 302 as a combination of 3D Surface Data Measurement Method 350 and Known Implant Measurement Method 370 which are both selected buy selector 302. In other words, Implant Angle Measurement Method 380 will be available when the combination of both methods 350 and 370 have been previously selected by the selector 302. In this way, the most accurate measurement data can be available based on the outputs of methods 350 and 370 to be further processed by method 380.

For a radiographic image 120 featuring an identified dental implant as the oral structure 125, an implant database with associated implant size measurements may be used to identify the angle at which the implant was oriented in relation to an x-ray sensor 312 when the image was produced. The distortion of implant dimensions on the radiograph compared with the true proportions of the implant will allow for the calculation of the angle and position of the implant in relation to the x-ray source and sensor. Comparison of the angle between the implant and x-ray source and adjacent dental crowns and the x-ray sources will allow for the determination of the angulation of the dental implant in relation to teeth and adjacent structures, including for example, restorations, bone structure, and periodontal ligaments. The implant model is identified using the Known Implant Measurement Method 370. The identified pixels representing the implant(s) in the image are identified and total distortion of the implant shape is calculated from the change in implant proportions as compared with implant's true dimensional proportions. Total distortion of implant is then used to calculate the angle at which the implant was oriented in relation to the x-ray sensor 312 when the radiographic image 120 image was produced.

The calculated angle between implant(s) identified in dental radiograph 120 and the x-ray source is compared with the calculated angle between adjacent teeth present in the dental radiograph 120 and the x-ray source from method 350, In order to calculate angle between implant(s) identified in dental radiograph and adjacent teeth present in the dental radiograph.

In step 382, pixels representing a dental implant within the radiographic image 120 as the oral structure 125 image are identified. In step 384, the outer border of the dental implant is identified. In step 386, the outer border is compared with the Dictionary of Projections 352 to determine the angle of the implant and the plane of the sensor 312 with respect to the x-ray source. In step 388, the position of the dental implant in relation to teeth by comparing the implant source angle to teeth source angle is determined. Given the detailed geometric information available about the dental implant and the angle of the sensor 312, the pixel to millimeter ratio 385 can then be determined with the highest accuracy.

Referring back to FIG. 5, the collective outputs of the selected combination of methods 304, 320, 350, and 370, and 380 comprise the sensor pixel to mm ratios 385, any of which can be selectively employed based on desired measurement accuracy and their availability from each method, along with the image metadata that is in terms of pixels, to produce a calibrated measurement 390 that provides desired measurements of the oral structures 125 in terms of millimeters. Depending on the available combination of methods 304, 320, 350, 370, and 380 to provide the sensor pixel to mm ratio 385, step 392 provides a measurement confidence indication which in turn is used to determine a threshold 394.

Confidence metrics are used to determine which tooth is used for calibration of relative to absolute measurements using various factors (e.g. ranked standard deviation of tooth anatomy for each given tooth type, presence of previous dental restoration, and pairwise analysis of ratios between available teeth within the image that may be used to complete the calibration to determine outliers and discard from calibration). Kalman filtering techniques may be used to incorporate multiple sources of information and make use of all available measurements even if they may be noisy. At least some of this information can be incorporated with a known uncertainty to weight their contribution. Confidence of calibration 392 is used to adjust threshold 394 for accepting or rejecting the presence of bone loss. Further use of ML techniques provided by training mechanism 140 may further enhance the reliability and confidence level of measurements based on further use of available inputs applied in various combinations of available information, such as data related to previous radiographic images, measurements, and oral structures for particular patients that take their historical information into account, as well as information on particular sensor types such as particular known characteristics that could create noise and associated mitigations.

The library 150 is collectively a data library that may be used to enable the various methods featured in the system 100 to be executed. The library 150 may be comprised of data from previous research, as well as data generated through execution of the system 100.

Types of information within the library 150 may include, but are not limited to:

1. X-Ray Sensor Database
Sensor names
Sensor size
Dimensions of effective areas (length and width)

| Dental Sensor Data | | | | |
|---|---|---|---|---|
| | Name | Manufacturer | Effective area Length | Effective area width |
| Sensor 1 | "33", size 2 | Schick | _._ mm | _._ mm |
| Sensor 2 | "Dream Sensor", size 0 | DentiMax | _._ mm | _._ mm |

2. Implant Database:
Implant names
Implant specifications
   Manufacturer
   Model name
   Years produced
   Dimensions
   Descriptive attributes
Once the implant is identified using the database, the pixel to mm ratio of the image can be determined.

3. Population-Based Anatomical Averages
Average dental crown dimensions

| Average Crown Mesiodistal Width at CEJ Level | | | |
|---|---|---|---|
| | Tooth #1 | Tooth #2 | etc. |
| Male | _._ mm | _._ mm | _._ mm |
| Female | _._ mm | _._ mm | _._ mm |

Average CEJ-bone level distance

| Average CEJ-Alveolar Crest Distance | | | |
|---|---|---|---|
| | Tooth #1 | Tooth #2 | etc. |
| Male | _._ mm | _._ mm | _._ mm |
| Female | _._ mm | _._ mm | _._ mm |

Average dental root dimensions

| Average Root Length | | | | | |
|---|---|---|---|---|---|
| | Tooth #3 palatal root | Tooth #3 mesiobuccal root | Tooth #3 distobuccal root | Tooth #4 buccal root | etc. |
| Male | _._ mm | _._ mm | _._ mm | _._ mm | _._ mm |
| Female | _._ mm | _._ mm | _._ mm | _._ mm | _._ mm |

Figure 13:
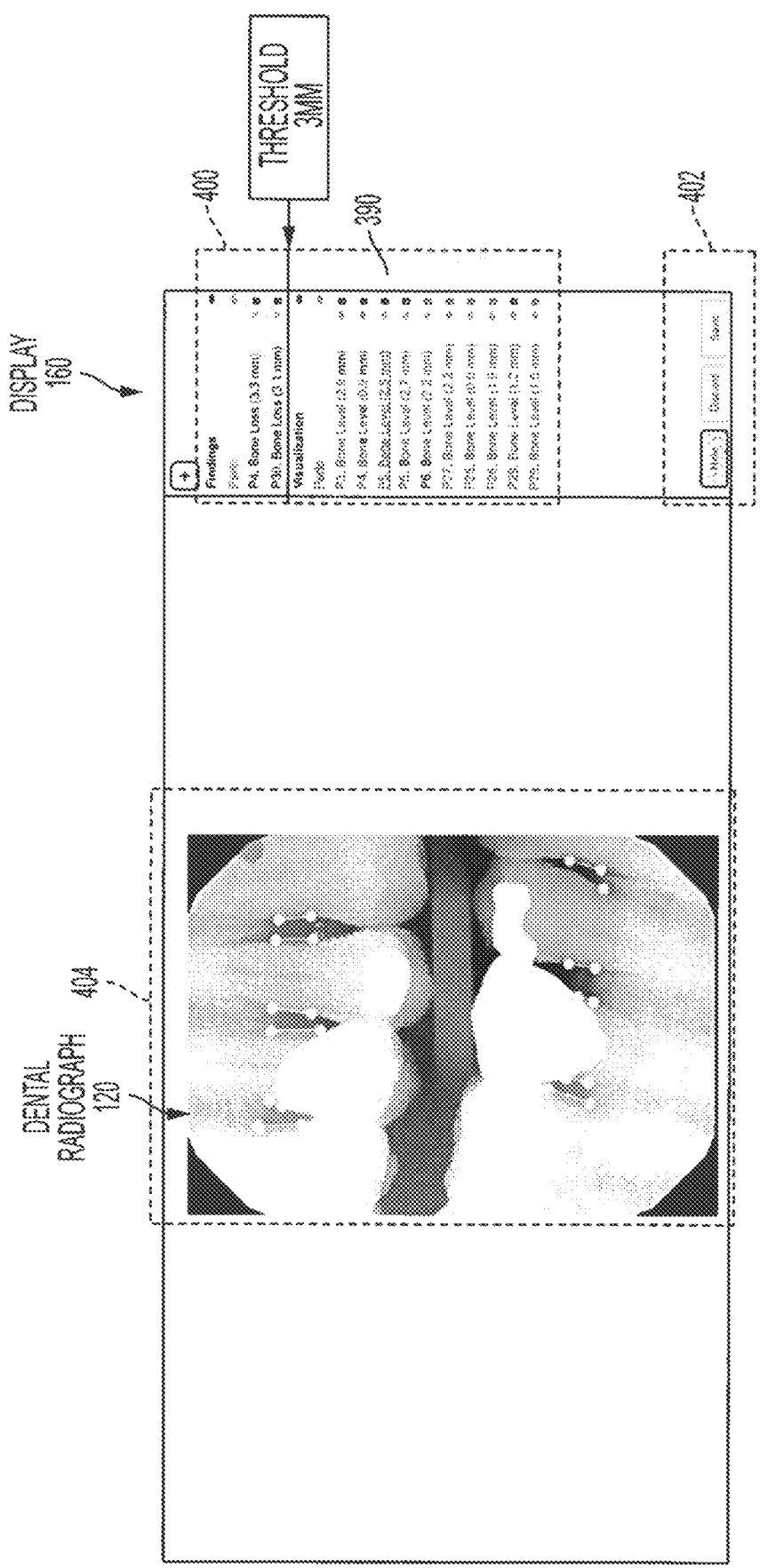
FIG. 13 is an example graphical user interface (GUI) screen for presenting desired calibrated measurements related to a radiograph image.

4. Patient-Specific Data
Previous 2-D radiographs
   Folder of 2-D image files (.jpg, .png, etc.)
   Table of Measurements gathered from processed images
Previous 3-D radiographs
   Folder of 3-D files (DICOM, NRRD, etc.)
   Table of Measurements gathered from processed images
Previous 3-D surface scans
   Folder of 3-D surface files (.stl)
   Table of Measurements gathered from processed images FIG. 13 is an example GUI (graphical user interface) screen on the display 160 for allowing a user to view the dental radiographic image 120 in a Display Area 404 that may include various oral structures 125. A set of graphical measurements may be superimposed on the dental radiographic image 120 in the display area 404 that correspond to a set of calibrated measurements 390 that are displayed in a data area 400. The set of calibrated measurements 390 may be divided according to the threshold 394 that is determined in the measurement processor 300. Alternatively, the GUI screen may provide further user controls such as the ability for the user to set the threshold 394 manually as shown by the THRESHOLD 3MM control. A user control area 402 includes various GUI screen functions that may include Hide, Discard, and Save related to the displayed measurement results.

Figure 14:
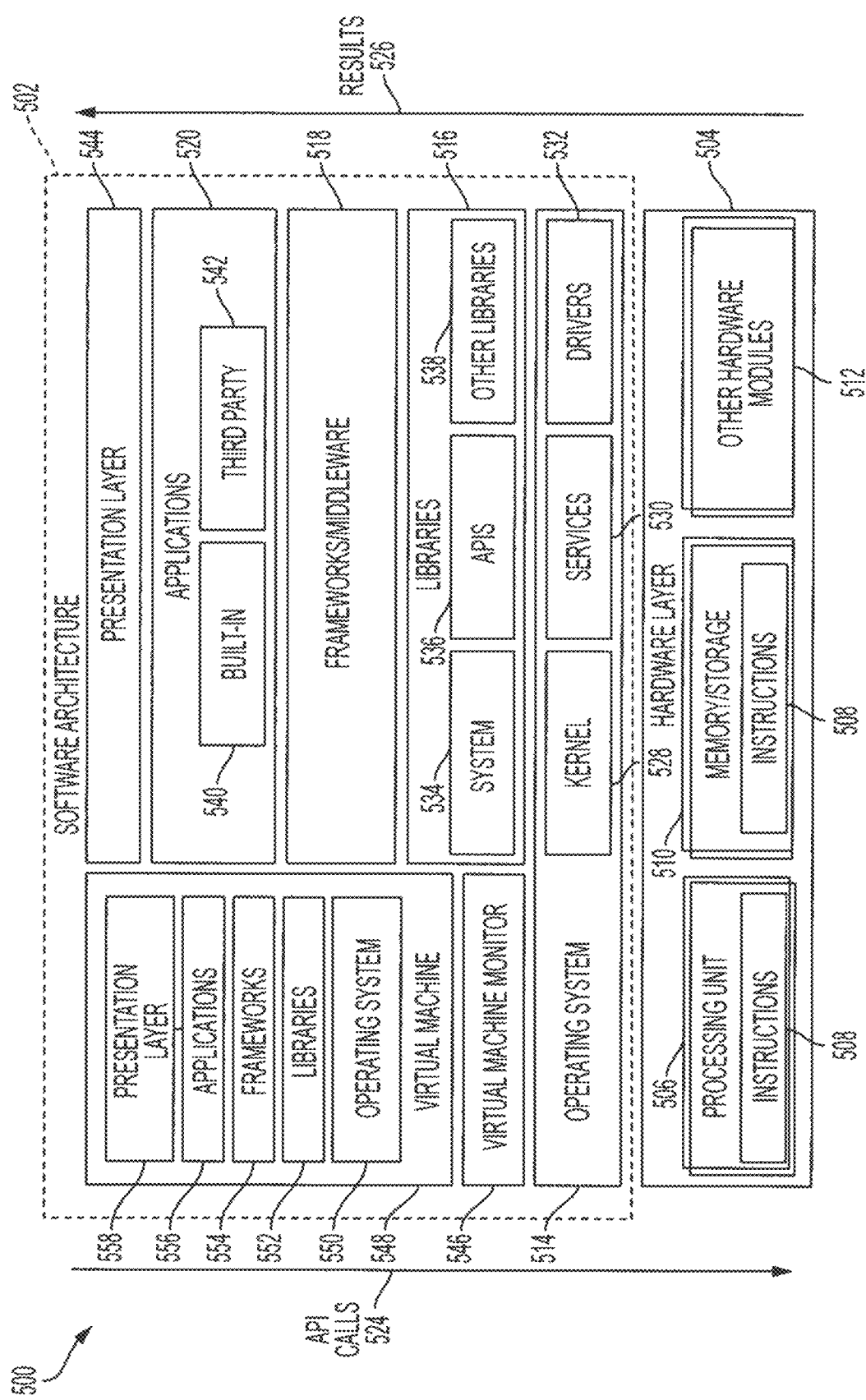
FIG. 14 is a block diagram illustrating an example software architecture, various portions of which may be used in conjunction with various hardware architectures herein described.

FIG. 14 is a block diagram 500 illustrating an example software architecture 502 that the system 100 may execute on, various portions of which may be used in conjunction with various hardware architectures herein described, which may implement any of the above-described features. FIG. 14 is a non-limiting example of a software architecture and it will be appreciated that many other architectures may be implemented to facilitate the functionality described herein. The software architecture 502 may execute on hardware such as client devices, native application provider, web servers, server clusters, external services, and other servers. A representative hardware layer 504 includes a processing unit 506 and associated executable instructions 508. The executable instructions 508 represent executable instructions of the software architecture 502, Including implementation of the methods, modules and so forth described herein.

The hardware layer 504 also includes a memory/storage 510, which also includes the executable instructions 508 and accompanying data. The hardware layer 504 may also include other hardware modules 512 that may include a graphics processing unit (GPU). Instructions 508 held by processing unit 508 may be portions of instructions 508 held by the memory/storage 510.

The example software architecture 502 may be conceptualized as layers, each providing various functionality. For example, the software architecture 502 may include layers and components such as an operating system (05) 514, libraries 516, frameworks 518, applications 520, and a presentation layer 544. Operationally, the applications 520 and/or other components within the layers may invoke API calls 524 to other layers and receive corresponding results 526. The layers illustrated are representative in nature and other software architectures may include additional or different layers. For example, some mobile or special purpose operating systems may not provide the frameworks/middleware 518.

The OS 514 may manage hardware resources and provide common services. The OS 514 may include, for example, a kernel 528, services 530, and drivers 532. The kernel 528 may act as an abstraction layer between the hardware layer 504 and other software layers. For example, the kernel 528 may be responsible for memory management, processor management (for example, scheduling), component management, networking, security settings, and so on. The services 530 may provide other common services for the other software layers. The drivers 532 may be responsible for controlling or interfacing with the underlying hardware layer 504. For instance, the drivers 532 may include display drivers, camera drivers, memory/storage drivers, peripheral device drivers (for example, via Universal Serial Bus (USB)), network and/or wireless communication drivers, audio drivers, and so forth depending on the hardware and/or software configuration.

The libraries 516 may provide a common infrastructure that may be used by the applications 520 and/or other components and/or layers. The libraries 516 typically provide functionality for use by other software modules to perform tasks, rather than rather than interacting directly with the OS 514. The libraries 516 may include system libraries 534 (for example, C standard library) that may provide functions such as memory allocation, string manipulation, file operations. In addition, the libraries 516 may include API libraries 536 such as media libraries (for example, supporting presentation and manipulation of image, sound, and/or video data formats), graphics libraries (for example, an OpenGL library for rendering 2D and 3D graphics on a display), database libraries (for example, SQLite or other relational database functions), and web libraries (for example, WebKit that may provide web browsing functionality). The libraries 516 may also include a wide variety of other libraries 538 to provide many functions for applications 520 and other software modules.

The frameworks 518 (also sometimes referred to as middleware) provide a higher-level common infrastructure that may be used by the applications 520 and/or other software modules. For example, the frameworks 518 may provide various graphic user interface (GUI) functions, high-level resource management, or high-level location services. The frameworks 518 may provide a broad spectrum of other APIs for applications 520 and/or other software modules.

The applications 520 include built-in applications 520 and/or third-party applications 522. Examples of built-in applications 520 may include, but are not limited to, a contacts application, a browser application, a location application, a media application, a messaging application, and/or a game application. Third-party applications 542 may include any applications developed by an entity other than the vendor of the particular system. The applications 520 may use functions available via OS 514, libraries 516, frameworks 518, and presentation layer 544 to create user interfaces to interact with users.

Some software architectures use virtual machines, as illustrated by a virtual machine 548. The virtual machine 548 provides an execution environment where applications/modules can execute as if they were executing on a hardware machine (such as the machine 600 of FIG. 6, for example). The virtual machine 548 may be hosted by a host OS (for example, OS 514) or hypervisor, and may have a virtual machine monitor 546 which manages operation of the virtual machine 548 and interoperation with the host operating system. A software architecture, which may be different from software architecture 502 outside of the virtual machine, executes within the virtual machine 548 such as an OS 550, libraries 552, frameworks 554, applications 556, and/or a presentation layer 558.

Figure 15:
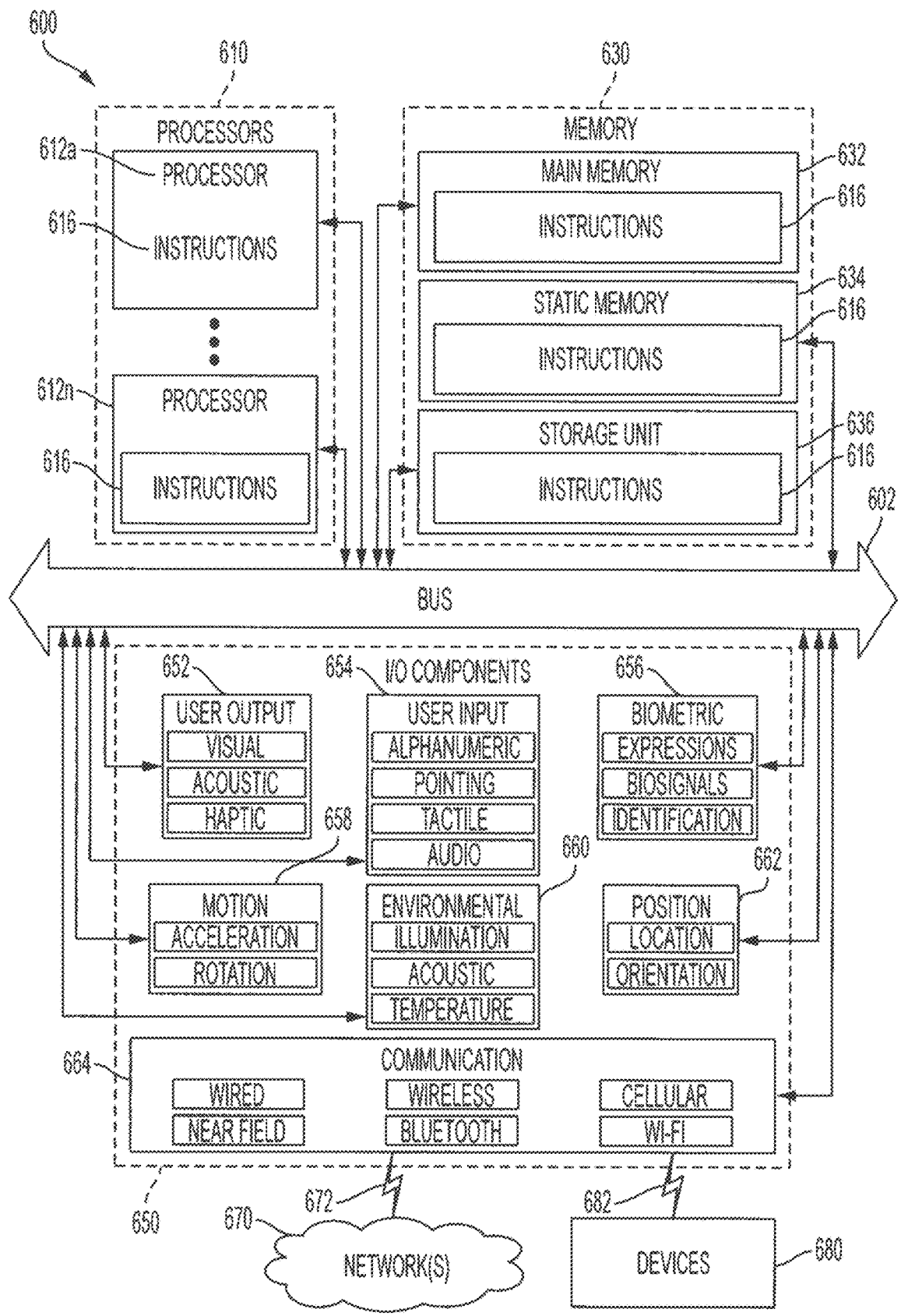
FIG. 15 is a block diagram illustrating components of an example machine configured to read instructions from a machine-readable medium and perform any of the features described herein.

FIG. 15 is a block diagram illustrating components of an example machine 600 configured to read instructions from a machine-readable medium (for example, a machine-readable storage medium) and perform any of the features described herein that the system 100 can execute instructions on. The example machine 600 is in a form of a computer system, within which instructions 616 (for example, in the form of software components) for causing the machine 600 to perform any of the features described herein may be executed. As such, the instructions 616 may be used to implement methods or components described herein. The instructions 616 cause unprogrammed and/or unconfigured machine 600 to operate as a particular machine configured to carry out the described features. The machine 600 may be configured to operate as a standalone device or may be coupled (for example, networked) to other machines. In a networked deployment, the machine 600 may operate in the capacity of a server machine or a client machine in a server-client network environment, or as a node in a peer-to-peer or distributed network environment. Machine 600 may be embodied as, for example, a server computer, a client computer, a personal computer (PC), a tablet computer, a laptop computer, a netbook, a set-top box (STB), a gaming and/or entertainment system, a smart phone, a mobile device, a wearable device (for example, a smart watch), and an Internet of Things (IoT) device. Further, although only a single machine 600 is illustrated, the term "machine" includes a collection of machines that individually or jointly execute the instructions 616.

The machine 600 may include processors 610, memory 630, and I/O components 650, which may be communicatively coupled via, for example, a bus 602. The bus 602 may include multiple buses coupling various elements of machine 600 via various bus technologies and protocols. In an example, the processors 610 (including, for example, a central processing unit (CPU), a graphics processing unit (GPU), a digital signal processor (DSP), an ASIC, or a suitable combination thereof) may include one or more processors 612a to 612n that may execute the instructions 616 and process data. In some examples, one or more processors 610 may execute instructions provided or identified by one or more other processors 610. The term "processor" Includes a multi-core processor including cores that may execute instructions contemporaneously. Although FIG. 6 shows multiple processors, the machine 600 may include a single processor with a single core, a single processor with multiple cores (for example, a multi-core processor), multiple processors each with a single core, multiple processors each with multiple cores, or any combination thereof. In some examples, the machine 600 may include multiple processors distributed among multiple machines.

The memory/storage 630 may include a main memory 632, a static memory 634, or other memory, and a storage unit 636, both accessible to the processors 610 such as via the bus 602. The storage unit 636 and memory 632, 634 store instructions 616 embodying any one or more of the functions described herein. The memory/storage 630 may also store temporary, intermediate, and/or long-term data for processors 610. The instructions 616 may also reside, completely or partially, within the memory 632 and 634, within the storage unit 636, within at least one of the processors 610 (for example, within a command buffer or cache memory), within memory at least one of I/O components 650, or any suitable combination thereof, during execution thereof. Accordingly, the memory 632 and 634, the storage unit 636, memory in processors 610, and memory in I/O components 650 are examples of machine-readable media.

As used herein, "machine-readable medium" refers to a device able to temporarily or permanently store instructions and data that cause machine 600 to operate in a specific fashion. The term "machine-readable medium," as used herein, does not encompass transitory electrical or electromagnetic signals per se (such as on a carrier wave propagating through a medium); the term "machine-readable medium" may therefore be considered tangible and non-transitory. Non-limiting examples of a non-transitory, tangible machine-readable medium may include, but are not limited to, nonvolatile memory (such as flash memory or read-only memory (ROM)), volatile memory (such as a static random-access memory (RAM) or a dynamic RAM), buffer memory, cache memory, optical storage media, magnetic storage media and devices, network-accessible or cloud storage, other types of storage, and/or any suitable combination thereof. The term "machine-readable medium" applies to a single medium, or combination of multiple media, used to store instructions (for example, instructions 616) for execution by a machine 600 such that the instructions, when executed by one or more processors 610 of the machine 600, cause the machine 600 to perform and one or more of the features described herein. Accordingly, a "machine-readable medium" may refer to a single storage device, as well as "cloud-based" storage systems or storage networks that include multiple storage apparatus or devices.

The I/O components 650 may include a wide variety of hardware components adapted to receive input, provide output, produce output, transmit information, exchange information, capture measurements, and so on. The specific I/O components 650 included in a particular machine will depend on the type and/or function of the machine. For example, mobile devices such as mobile phones may include a touch input device, whereas a headless server or IoT device may not include such a touch input device. The particular examples of I/O components illustrated in FIG. 6 are in no way limiting, and other types of components may be included in machine 600. The grouping of I/O components 650 are merely for simplifying this discussion, and the grouping is in no way limiting. In various examples, the I/O components 650 may include user output components 652 and user input components 654. User output components 652 may include, for example, display components for displaying information (for example, a liquid crystal display (LCD) or a projector), acoustic components (for example, speakers), haptic components (for example, a vibratory motor or force-feedback device), and/or other signal generators. User input components 654 may include, for example, alphanumeric input components (for example, a keyboard or a touch screen), pointing components (for example, a mouse device, a touchpad, or another pointing instrument), and/or tactile input components (for example, a physical button or a touch screen that provides location and/or force of touches or touch gestures) configured for receiving various user inputs, such as user commands and/or selections.

In some examples, the I/O components 650 may include biometric components 656 and/or position components 662, among a wide array of other environmental sensor components. The biometric components 656 may include, for example, components to detect body expressions (for example, facial expressions, vocal expressions, hand or body gestures, or eye tracking), measure biosignals (for example, heart rate or brain waves), and identify a person (for example, via voice-, retina-, and/or facial-based identification). The position components 662 may include, for example, location sensors (for example, a Global Position System (GPS) receiver), altitude sensors (for example, an air pressure sensor from which altitude may be derived), and/or orientation sensors (for example, magnetometers).

The I/O components 650 may include communication components 664, implementing a wide variety of technologies operable to couple the machine 600 to network(s) 670 and/or device(s) 680 via respective communicative couplings 672 and 682. The communication components 664 may include one or more network interface components or other suitable devices to interface with the network(s) 670. The communication components 664 may include, for example, components adapted to provide wired communication, wireless communication, cellular communication, Near Field Communication (NFC), Bluetooth communication, wi-fi, and/or communication via other modalities. The device(s) 680 may include other machines or various peripheral devices (for example, coupled via USB).

In some examples, the communication components 664 may detect identifiers or include components adapted to detect identifiers. For example, the communication components 664 may include Radio Frequency Identification (RFID) tag readers, NFC detectors, optical sensors (for example, one- or multi-dimensional bar codes, or other optical codes), and/or acoustic detectors (for example, microphones to identify tagged audio signals). In some examples, location information may be determined based on information from the communication components 662, such as, but not limited to, geo-location via Internet Protocol (IP) address, location via Wi-Fi, cellular, NFC, Bluetooth, or other wireless station identification and/or signal triangulation.

While various embodiments have been described, the description is intended to be exemplary, rather than limiting, and it is understood that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

Generally, functions described herein (for example, the features illustrated in FIG. 1) can be implemented using software, firmware, hardware (for example, fixed logic, finite state machines, and/or other circuits), or a combination of these implementations. In the case of a software implementation, program code performs specified tasks when executed on a processor (for example, a CPU or CPUs). The program code can be stored in one or more machine-readable memory devices. The features of the techniques described herein are system-independent, meaning that the techniques may be implemented on a variety of computing systems having a variety of processors. For example, implementations may include an entity (for example, software) that causes hardware to perform operations, e.g., processors functional blocks, and so on. For example, a hardware device may include a machine-readable medium that may be configured to maintain Instructions that cause the hardware device, including an operating system executed thereon and associated hardware, to perform operations. Thus, the instructions may function to configure an operating system and associated hardware to perform the operations and thereby configure or otherwise adapt a hardware device to perform functions described above. The instructions may be provided by the machine-readable medium through a variety of different configurations to hardware elements that execute the instructions.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows, and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of Inquiry and study except where specific meanings have otherwise been set forth herein.

Relational terms such as first and second and the like may be used solely to distinguish one entity or action from another without necessarily requiring or Implying any actual such relationship or order between such entities or actions. The terms "comprises," "comprising," and any other variation thereof, are intended to cover a non-exclusive Inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

The Abstract of the Disclosure is provided to allow the reader to quickly identify the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that any claim requires more features than the claim expressly recites. Rather, as the following claims reflect, inventive subject matter lies in less than all features of a single disclosed example. Thus, the following claims are hereby Incorporated into the Detailed Description, with each claim standing on its own as a separately claimed subject matter.

What is claimed is:

1. A data processing system comprising:
   a processor; and
   a memory in communication with the processor, the memory comprising executable instructions that, when executed by, the processor, cause the data processing system to perform functions of:
   receiving a dental radiographic image that includes an oral structure;
   selecting a segmenter and an object detector;
   predicting masks and points of the oral structure using the segmenter and the object detector;
   providing image metadata comprising the masks and points and the dental radiographic image to a selector;
   selecting by the selector at least one measurement method of a set of measurement methods according to the dental radiographic image and the Image metadata;
   calculating a sensor pixel to mm (millimeter) ratio using the measurement method; and
   calculating a calibrated measurement of the oral structure using the sensor pixel to mm ratio and the image metadata.

2. The data processing system of claim 1, wherein the instructions further cause the processor to cause the data processing system to perform functions of:
   detecting an orientation of the dental radiographic image; and
   if the orientation is incorrect, correcting the orientation.

3. The data processing system of claim 1, the set of measurement methods comprising:
   a known sensor measurement method;
   an oral structure measurement method;
   a 3D surface data measurement method;
   a known implant measurement method; and
   an implant angle measurement method.

4. The data processing system of claim 1, wherein the instructions further cause the processor to cause the data processing system to perform functions of:
   receiving data from a library, the library comprising at least one of:
   an X-ray sensor database;
   an Implant database;
   a population based anatomical averages database; and
   a patient specific database.

5. The data processing system of claim 4, wherein the instructions further cause the processor to cause the data processing system to perform functions of:
   determining a confidence metric of the calibrated measurement; and
   adjusting a threshold based on the confidence metric.

6. The data processing system of claim 4, wherein the Instructions further cause the processor to cause the data processing system to perform functions of:
   providing a machine-learning based training mechanism to train the segmenter and the object detector to identify at least one of Individual teeth, restorations, implants, cemento enamel Junction (CEJ) points, and bone points.

7. The data processing system of claim 1, wherein the instructions further cause the processor to cause the data processing system to perform functions of:
enabling a graphical user interface to display the radiographic image and the calibrated measurement.

8. The data processing system of claim 7, wherein the Instructions further cause the processor to cause the data processing system to perform functions of:
displaying a plurality of the calibrated measurements according to the threshold.

9. The data processing system of claim 1, wherein the instructions further cause the processor to cause the data processing system to perform functions of:
determining an Image type of the dental radiographic image; and
based on the image type, selecting the segmenter and the object detector from a set of segmenters and object detectors.

10. A method for providing a calibrated measurement of an oral structure in a dental radiograph image comprising:
receiving a dental radiographic Image that includes the oral structure;
selecting a segmenter and an object detector;
predicting masks and points of the oral structure using the segmenter and the object detector;
providing image metadata comprising the masks and points and the dental radiographic image to a selector;
selecting by the selector at least one measurement method of a set of measurement methods according to the dental radiographic image and the image metadata;
calculating a sensor pixel to mm (millimeter) ratio using the measurement method; and
calculating a calibrated measurement of the oral structure using the sensor pixel to mm ratio and the image metadata.

11. The method of claim 10 further comprising:
detecting an orientation of the dental radiographic image; and
if the orientation is incorrect, correcting the orientation.

12. The method of claim 10 wherein the set of measurement methods further comprises:
a known sensor measurement method;
an oral structure measurement method;
a 3D surface data measurement method;
a known implant measurement method; and
an implant angle measurement method.

13. The method of claim 10 further comprising:
receiving data from a library, wherein the library further comprises at least one of:
an X-ray sensor database;
an implant database;
a population based anatomical averages database; and
a patient specific database.

14. The method of claim 13 further comprising:
determining a confidence metric of the calibrated measurement; and
adjusting a threshold based on the confidence metric.

15. The method of claim 13 further comprising:
providing a machine-learning based training mechanism to train the segmenter and the object detector to identify at least one of individual teeth, restorations, implants, cemento enamel junction (CEJ) points, and bone points.

16. The method of claim 10 further comprising:
enabling a graphical user interface to display the radiographic image and the calibrated measurement.

17. The method of claim 16 further comprising:
displaying a plurality of the calibrated measurements according to the threshold.

18. The method of claim 10, further comprising:
determining an image type of the dental radiographic image; and
based on the image type, selecting the segmenter and the object detector from a set of segmenters and object detectors.

* * * * *